(12) United States Patent
Stedman et al.

(10) Patent No.: US 7,771,993 B2
(45) Date of Patent: Aug. 10, 2010

(54) MICROUTROPHIN AND USES THEREOF

(75) Inventors: Hansell H. Stedman, Norristown, PA (US); Leonard T. Su, Seattle, WA (US); Marilyn A. Mitchell, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 737 days.

(21) Appl. No.: 10/586,890

(22) PCT Filed: Jan. 21, 2005

(86) PCT No.: PCT/US2005/001768

§ 371 (c)(1),
(2), (4) Date: Jul. 21, 2006

(87) PCT Pub. No.: WO2005/118611

PCT Pub. Date: Dec. 15, 2005

(65) Prior Publication Data

US 2008/0242623 A1 Oct. 2, 2008

Related U.S. Application Data

(60) Provisional application No. 60/538,877, filed on Jan. 23, 2004.

(51) Int. Cl.
 C12N 15/00 (2006.01)
 C07H 21/04 (2006.01)
(52) U.S. Cl. .................................. 435/320.1; 536/23.1
(58) Field of Classification Search ........................ None
 See application file for complete search history.

(56) References Cited

U.S. PATENT DOCUMENTS

| 6,518,413 | B1 * | 2/2003 | Tinsley et al. ............... 536/23.1 |
| 2003/0171312 | A1 | 9/2003 | Xiao |
| 2003/0216332 | A1 | 11/2003 | Chamberlain et al. |

FOREIGN PATENT DOCUMENTS

WO   WO 01/25461 A1   4/2001

OTHER PUBLICATIONS

Amann et al, Utrophin Lacks the Rod Domain Actin Binding Activity of Dystrophin, The Journal of Biological Chemistry, vol. 274, No. 50, pp. 3575-35380, (Dec. 10, 1999).
Baranov et al, The Current State and Prospects of the Gene Therapy of Duchenne Muscular Dystrophy Worldwide and in Russia, Russian Journal of Genetics, vol. 37, No. 8, pp. 868-875, (Aug. 2001).
Gilbert et al, Improved Performance of a Fully Gutted Adenovirus Vector Containing Two Full-Length Dystrophin cDNAs Regulated by a Strong Promoter, Molecular Therapy, vol. 6, No. 4, (Oct. 2002).
Guo et al, Cloning and Expression of Full length Mouse Utrophin: the Differential association of Utrophin and Dystrophin with AChR Clusters, FEBS Letters, 398, (2-3), pp. 259-264, (Dec. 1996).
Perkins et al, The Role of Utrophin in the Potential Therapy of Duchenne Muscular Dystrophy, Neuromuscular Disorders, 12, Suppl. 1, pp. S78-S89, (Oct. 2002).
Squire at al, Prevention of Pathology in mdx Mice by Expression of Utrophin: Analysis Using an Inducible Transgenic Expression System, Human Molecular Genetics, vol. 11, No. 26, pp. 3333-3344, (Dec. 2002).
Tinsley et al, Primary Structure of Dystrophin-Related Protein, Nature, vol. 360, pp. 591-593, (Dec. 10, 1992).
Van Deutekom et al, Advances in Duchenne Muscular Dystrophy Gene Therapy, Nature Reviews Genetics, vol. 4, pp. 774-783, (Oct. 2003).
Wilson et al, Up71 and Up140, Two Novel Transcripts of Utrophin that are Homologues of Short Forms of Dystrophin, Human Molecular Genetics, vol. 8, No. 7, pp. 1271-1278, (Jul. 1999).
Winder et al, Dystrophin and Utrophin: the missing links!, FEBS Letters, 369, pp. 27-33, (Aug. 1, 1995).

* cited by examiner

*Primary Examiner*—Suzanne M. Noakes
(74) *Attorney, Agent, or Firm*—Howson & Howson LLP

(57) ABSTRACT

A microutrophin containing a utrophin having internal deletions (relative to a native utrophin) in the hinge regions and a C-terminal deletion is provided. Also provided are vectors and compositions useful for delivering the microutrophin for the treatment of muscular disorders, including Duchenne Muscular Dystrophy.

14 Claims, 30 Drawing Sheets

FIG. 1A

```
Mouse Microutro      1  ATGGCCAAGTATGGGGACCTTGAAGCCAGGCCTGATGATGGGCAGAACGA   50
Human Microutro      1  ATGGCCAAGTATGGAGAGAACATGGAAGCCAGTCCTGACAATGGGCAGAACGA 50
Canine Microutr      1  ATGGCCAAGTATGGAGAGAACATGAAGCCAGTCCTGATAATGGGCAGAACGA   50
                        ****************** **  * ************

Mouse Microutro     51  ATTCAGTGACATCATTAAGTCCAGATCTGATGAACACAATGATGTACAGA   100
Human Microutro     51  ATTCAGTGATATCATTAAGTCCAGATCTGATGAACACGTACAGA         100
Canine Microutr     51  ATTCAGTGACATCATTAAGTCCAGATCTGATGAACATGACGTGCAGA      100
                        ********* ************************  ** ****

Mouse Microutro    101  AGAAAACCTTTACCAAATGGATAAACGCTCGATTTTCCAAGAGTGGGAAA   150
Human Microutro    101  AGAAAACCTTTACCAAATGATAATGCTCGATTTCAAAGAGTGGGAAA      150
Canine Microutr    101  AGAAAACCTTTACCAAATGGATCAATGCGCGATTTCAAAGAGTGGGAAA    150
                        ****************** **  ** *********  ***********

Mouse Microutro    151  CCACCCATCAGTGATATGTTCTCAGACCTCAAAGATGGGAGAAAGCTCTT   200
Human Microutro    151  CCACCCATCAATGATATGTTCACAGACCTCAAAGATGAAGGAAGCTATT    200
Canine Microutr    151  CCACCCATCAATGATATGTTCACAGACCTCAAAGATGGAAGGAAGCTCCT   200
                        **********  *********  ************** ** ******

Mouse Microutro    201  GGATCTTCTCGAAGGCCTCACAGGAACATCATTGCCAAAGGAACGTGGTT   250
Human Microutro    201  GGATCTTCTAGAAGGCCCTCACAGGAACATCACTGCCAAAGGAACGTGGTT  250
Canine Microutr    201  GGATCTTCTGGAAGGCCTCACAGGAACATCACTGCCAAAGGAACGTGGTT   250
                        ********* ******************* ******************
```

FIG. 1B

```
Mouse Microutro   251  CCACAAGGGTGCATGCCTTAAACAATGTCAACCGAGTGCTACAGGTTTTA  300
Human Microutro   251  CCACAAGGGTACATGCCTTAAATAACGTCAACAGAGTGCTGCAGGTTTTA  300
Canine Microutr   251  CCACAAGGGTACATGCTTTAAATAATGTCAACAGAGTGCTGCAGGTTTTG  300
                      ************  ** ******  **** *** ****  *********

Mouse Microutro   301  CATCAGAACAATGTGGACTTGGTGAATATTGGAGGCACGGACATTGTGGC  350
Human Microutro   301  CATCAGAACAATGTGGAATTAGTGAATAGTAGGGGGAACTGACATTGTGGA  350
Canine Microutr   301  CATCAGAATAATGTGGATTTAGTGAATAGTAGGAGGAACTGACATTGTAGA  350
                      ******** ******** ** ******  **  ** ** ********  *

Mouse Microutro   351  TGGAAATCCCAAGCTGACTTTAGGGTTACTCTGGAGCATCATTCTGCACT  400
Human Microutro   351  TGGAAATCACAAACTGACTTTGGGGTTACTGACTTTGGAGCATCATTTTGCACT  400
Canine Microutr   351  TGGAAATCACAAACTGACTTTGGGATTACTTTGGAGCATCATTTTGCACT  400
                      ******** *** ****** **  ****  ** *********  *****

Mouse Microutro   401  GGCAGGTGAAGGATGTCATGAAAGATATCATGTCAGACCTGCAGCAGACA  450
Human Microutro   401  GGCAGGTGAAAGATGTCATGAAGGATGTCATGTCGGAGCTGCAGCAGACG  450
Canine Microutr   401  GGCAGGTAAAAGATGTCATGAAAGATGTCATGTCATCAGACCTGCAGCAGACA  450
                      *******  * ***********  ***  ***** *** *********

Mouse Microutro   451  AACAGCGAGAAGATCCTGCTGAGCTGGGTGCGGCAGACCACCAGGCCCTA  500
Human Microutro   451  AACAGTGAGAAGATCCTGCTCAGCTGGGTGCGTGCTCAGACCAGCCCCTA  500
Canine Microutr   451  AACAGTGAGAAGATCCTACTGAGCTGGGTGCGCCAGCCAGTCTAGGCCGTA  500
                      *****  ****** *  **  ***********   *  ***    ** **
```

FIG. 1C

```
Mouse Microutro    501 CAGTCAAGTCAACGTCCTCAACTTCACCACCAGCTGGACCGATGGACTCG 550
Human Microutro    501 CAGCCAAGTCAACGTCCTCAACTTCACCACCAGCTGGACAGATGGACTCG 550
Canine Microutr    501 CAGCCAGTCAACGTCCTCAACTTCACCACCAGCTGGACAGATGGACTGG 550
                       *** ** ************************** ****** ******

Mouse Microutro    551 CGTTCAACGCCGTGCTCCACCGGCACAAACCAGATCTCTTTGACTGGGAC 600
Human Microutro    551 CCTTTAATGCTGTGCTCCTCCACCGACATAAACCTGATCTCTTCAGCTGGGAT 600
Canine Microutr    551 CCTTTAATGCTGTGCTCCTCCACCGACATAAACCTGATCTCTTCAGCTGGGAT 600
                       * ** ** ** ******  ***** ** ***** ********  ******

Mouse Microutro    601 GAGATGGTCAAAAATGTCCCCAATTGAGAGACTTGACCATGCTTTTGACAA 650
Human Microutro    601 AAAGTTGTCAAAAATGTCACCAATTGAGAGACTTGAACATGCCTTCAGCAA 650
Canine Microutr    601 AGAGTTGTCAAAAATGTCCCCAATTGAGAGACTTGAACATGCCTTCAGCAA 650
                        * ************ ***************** ***** **  ****

Mouse Microutro    651 GGCCCACACTTCTTTGGGAATTGAAAAGCTCCTAAGTCCTGAAACTGTTG 700
Human Microutro    651 GGCTCAAACTTATTTGGGAATTGAAAAGCTGTTAGATCCTGAAGATGTTG 700
Canine Microutr    651 AGCTCAAACTTATTTGGGAATTGAAAAGCTGTTAGATCCTGAAGATGTTG 700
                        ** ** **** **************** *  ********  *****

Mouse Microutro    701 CTGTGCATCTCCCTGACAAGAAATCCATAATTATGTATTTAACGTCTCTG 750
Human Microutro    701 CCGTTCGGCTTCCTGACAAGAAATCCATAATTATGTATTTAACATCTTTG 750
Canine Microutr    701 CCGTTCAACTTCCTGACAAGAAATCCATAATTATGTATTTAACATCTTTG 750
                       * **  *  ****************************** *** **
```

FIG. 1D

```
Mouse Microutro    751 TTTGAGGTGCTGCTTCCTCAGCAAGTCACGATAGATGCCATCCGAGAGGTGGA  800
Human Microutro    751 TTTGAGGTGCTACCTCCTCAGCAAGTCAAGTCACCATAGACGCCATCCGTGAGGTAGA  800
Canine Microutr    751 TTTGAGGTGCTGCTTCCTCAGCAAGTCACTCTAGATGCCATCCGTGAAGTAGA  800
                       ***************** ** **   **    *  ** *******  ** **

Mouse Microutro    801 GACTCTCCCAAGGAAGTATAAGAAAGAATGTGAAGAGGAAGAAATTCATA  850
Human Microutro    801 GACACTCCCAAGGAAGTAAATATAAAAAAGAATGTGAAGAAGAGGCAATTAATA  850
Canine Microutr    801 GACACTCCCAAGGAAGTAAATATAAGAAAGAATGTGAAGAAGGAGATTAGTA  850
                       *** ************   ***       * ****** **  *** **  **

Mouse Microutro    851 TCCAGAGTGCAGTGCTGGCAGAGGAAGGCCAGAGTCCCCCGAGCTGAGACC  900
Human Microutro    851 TACAGAGTACAGCGCCTGAGGGAGGAGCATGAGAGTCCCCCGAGCTGAAACT  900
Canine Microutr    851 TACAGAGCTCAGCCAGCGCCGCCAGAGGAGGAGCATGAGTGTCCCGGAGCTGAAACC  900
                       * *****  ***   * *  * ** *** ** ***  ******* ****

Mouse Microutro    901 CCTAGCACCGTCACTGAAGTGGACATGGATTTGGACAGCTACCAGATAGC  950
Human Microutro    901 CCCAGCACTACTGTCACTGAGGTCGACATGGATCGATCTGGACAGCTATCAGATTGC  950
Canine Microutr    901 CCCAGCACTGTCACTGTCACTGAAGTTGACACGGATCTGGACAGCTATCAGATAGC  950
                       ** *****   ** ***** ** *** **** * ********* ***** **

Mouse Microutro    951 GCTAGAGGAAGTGCTGACCGTGCTGCTGTCCGCGGAGGACACGTTCCAGG  1000
Human Microutro    951 GTTGGAGGAAGTGCTGACCGTGCTGCTTGCTTTCTGCTGAGGACACTTTCCAGG  1000
Canine Microutr    951 ACTGGAGGAAGTGCTGACCTGGTTGCTTTCTGCCGAGGACACTTTCCAGG  1000
                         * ****************  **** *** ****** ***** *****
```

FIG. 1E

```
Mouse Microutro   1001  AGCAACAATGACATTTCTGATGATGTCGAAGAAGTCAAAGAGCAGTTTGCT  1050
Human Microutro   1001  AGCAGGATGATATTTCTGATGATGTTGAAGAAGTCAAAGACCAGTTTGCA  1050
Canine Microutr   1001  AGCAGGATGACATTTCTGATGATGTAGAAGAAGTCAAAGAGCAGTTTACT  1050
                        ****  ****  ************  ****** ********* ****** *

Mouse Microutro   1051  ACCCATGAAACTTTTATGATGGAGCTGACAGCACACCAGAGCAGCAGTGGG  1100
Human Microutro   1051  ACCCATGAAGCTTTTATGATGGAGCTGACTGCACACCAGAGCAGCAGTGGG  1100
Canine Microutr   1051  ACCCATGAAGCTTTTATGATGGAGCTGACAGCACACCAGAGCAGCAGTGGG  1100
                        ********* ******************* ***************** *****

Mouse Microutro   1101  GAGCGTCCTGCAGGCTGGCAACCAGCTGATGACAAGGACTCTGTCCA  1150
Human Microutro   1101  CAGCGTCCTGCAGGCAGGCAGCAACCAACTGATAACACAAGGAACTCTGTCAG  1150
Canine Microutr   1101  CAGTGTCCTGCAGGCAGGCAAACCAGCTGATAACGCAAGGAACTCTGTCAG  1150
                         ** ********** *** * *****  *****  ** ****** *********

Mouse Microutro   1151  GAGAGGAGGAGTTTGAGATCCAGGAACAGATGACCTTGCTGAATGCAAGG  1200
Human Microutro   1151  ACGAAGAAGAATTTGAGATTCAGGAACAGATGACCCTGCTGAATGCTAGA  1200
Canine Microutr   1151  ATGAGGAGGAAATTTGAAATTCAGGAACAAATGACCCTGCTAAATGCTAGA  1200
                        * ** ** ** * **** ** ******** ***** ***** ***** *

Mouse Microutro   1201  TGGGAGGCGCTCCGGGTGGAGAGGCAGTCCCGGCTGCACGA  1250
Human Microutro   1201  TGGGAGGCTCTTAGGGTGGAGAGCATGGAGACAGTCCCGGCTGCACGA  1250
Canine Microutr   1201  TGGGAGGCACTCAGGGTGGATAGTATGAACAGACAGTCCCGGCTGCATGA  1250
                        ********  **  ***** ** * **  ** *  * ************  *
```

FIG. 1F

```
Mouse Microutro   1251 CGCTCTCTGATGGAGCTGCAGAAGAAACAGCTGCAGCAGCTCTCAAGCTGGC 1300
Human Microutro   1251 TGTGCTGATGGAACTGCAGAAGAAGCAACTGCAGCAGCTCTCCGCCTGGT 1300
Canine Microutr   1251 TGTGTTGATGGAACTACAAAAGAAGCAGTTGCAACAGCTCTGCCTGGT 1300
                       *   *   ** *********  **  *** **  ****** **  ****

Mouse Microutro   1301 TGGCCCTCACAGAGAGCGCATTCAGAAGATGGAGAGCCTCCCGCTGGT 1350
Human Microutro   1301 TAACACTCACAGAGAGGAGCGCATTCAGAAGATGGAAACTTGCCCCCTGGAT 1350
Canine Microutr   1301 TAACACTCACAGAGAAGAACGCATTCAGAAGATGGAAACCTGCCCCCTGGAT 1350
                         *  *************   * *************  *   **** *

Mouse Microutro   1351 GATGACCTGCCCTCCCTGCAGAAGCTGCTTCAAGAACATAAAAGTTTGCA 1400
Human Microutro   1351 GATGATGTAAAAATCTCTACAAAAGCTGCTAGAAGAACATAAAAGTTTGCA 1400
Canine Microutr   1351 GATGATTTAAAAATCCCTACAAAAGCTACTAGAAGATCATAAACGTTTGCA 1400
                       *****   *  ***  ** ** *** **  * ****  ***** ******

Mouse Microutro   1401 AAATGACCTTGAAGCTGAACAGGTGAAGGTAAATTCCTTAACTCACATGG 1450
Human Microutro   1401 AAGTGATCTTGAGGCTGAACAGGTGAAAGTAAATTCACTCACATGG 1450
Canine Microutr   1401 AAATGATCTTGAGGCGGAACAGGTGAAGGTAAATTCACTAACACACATGG 1450
                       ** *** ****** ** *********  ********* **  ******

Mouse Microutro   1451 TGGTGATTGTGGATGAAAACAGTGGGGAGAGTGCCACAGCTCTTCTGAA 1500
Human Microutro   1451 TGGTCATTGTTGATGAAAACAGTGGTGAGAGCGCTACAGCTATCCTAGAA 1500
Canine Microutr   1451 TGGTGATTGTTGATGAAAACAGTGAGAGTGCCACTGCTGTTCTGAA 1500
                       **** ***** ************  ***** ** *** * ** ****
```

FIG. 1G

```
Mouse Microutro  1501 GATCAGTTACAGAAACTGGGTGAGCGCTGGACAGCTGTATGCCGCTGGAC 1550
Human Microutro  1501 GACCAGTTACAGAAACTTGGTGAGCGCTGGACAGCTGTATGCCGTTGGAC 1550
Canine Microutr  1501 GATCAGTTACAGAAACTTGGTGAACGCTGGACAGCAGTGTGCCGTTGGAC 1550
                      ** ************ ** ********** *** ** ********

Mouse Microutro  1551 TGAAGAACGTTGGAACAGGTTGCAAGAAATCAGTATTCTGTGGCAGGAAT 1600
Human Microutro  1551 TGAAGAACGCTGGAATAGGTTACAAGAATCAATCAATAATATATTGTGGCAGGAAT 1600
Canine Microutr  1551 AGAGGAACGTTGGAGTAGGCTACAAGAATTAATATATATTGTGGCAGGAAT 1600
                        * ***** **** *** * ***** * ** ** ***********

Mouse Microutro  1601 TATTGGAAGAGCAGTGTCTGTTGGAGGCTTGGCTCACCGAAAAGGAAGAG 1650
Human Microutro  1601 TATTGGAAGAACAGTGTGCTTGTTGTTGAAAGCTTGGTTAACCGAAAAGAAGAG 1650
Canine Microutr  1601 TATTAGAAGAACAGTGTGCTTGTTGTTGAAAGCTTGGCTAACTGAAAAGAAGAG 1650
                      **** ****** ***** ***** * ** **** * *** ******* ***

Mouse Microutro  1651 GCTTTGGATAAAGTTCAAACCAGCAACTTTAAAGACCAAGAAGGAACTAAG 1700
Human Microutro  1651 GCTTTAAATAAAGTTCCAGACAAGCAACTTCAAAGACCAAAAAGGAACTAAG 1700
Canine Microutr  1651 GCCTTAAATAAAGTCCAGACGAGCAACTTCAAAGACCAAAAAGGAACTAAG 1700
                      ** ** ******** ** ** ******** ********* ********

Mouse Microutro  1701 TGTCAGTGTCCGGCGTCTGGCTATATTGAAGGAAGACATGGAAATGAAGA 1750
Human Microutro  1701 TGTCAGTGTTCGACGTCTGGCTATTTGAAGGAAGACATGGAAATGAAGC 1750
Canine Microutr  1701 TGTCAGCATCCGACCGATTGGCTATTTTGAAGGAAGACATGGAAATGAAAC 1750
                      ****** * ** * ** ***** ** *********************
```

FIG. 1H

```
Mouse Microutro    1751 GGCAGAGACTCTGGATCAACTGAGTGAGATTGGCCAGGATGTGGGCCAATTA 1800
Human Microutro    1751 GTCAAACATTGGATCAGCTGAGTGAGATTGGCCAGGATGTGAGATTGGGACAATTA 1800
Canine Microutr    1751 GTCAGGCATTGGATCAGCTGAGTGAGATTGGCCAGGATGTGGGCCAATTA 1800
                        *  *    ************ *************** ************

Mouse Microutro    1801 CTCAGTAATCCCAAGGCATCTAAGAAGATGAACAGTGACTCTGAGGAGCT 1850
Human Microutro    1801 CTTGATAATCCCAAGGCATCTAAGAAGATCAACAGTCAGAGGAACT 1850
Canine Microutr    1801 GTTGATAATCCCAAGGCATCTAAGAAGATCAACAGTGACTCAGAGAACT 1850
                          * ************************** ***** ********* **

Mouse Microutro    1851 AACACAGAGATGGGATTCTCTGGTTCAGAGACTCGAAGACTCTTCTAACC 1900
Human Microutro    1851 GACTCAAAGATGGGATTCTTTGGTTCAGAGACTAGAAGATTCCTCCAACC 1900
Canine Microutr    1851 AACTCAGAGATGGGATTCTTTGGTTCAGAGACTAGAAGATTCCTCTAGCC 1900
                        ** ** ************* ************ ***** ** ** * **

Mouse Microutro    1901 AGGTGACTCAGGCGGTAGCGAAGCTCGGCATGTCCCAGATTCCACAGAAG 1950
Human Microutro    1901 AGGTGACTCAGCTGTAGCAAAGCTGGGGATGTCTCAGATTCCTCAGAAG 1950
Canine Microutr    1901 AGGTGACTCAGCTGTGTGCAAAGCTGGGATGTCCCAAATTCCTCAGAAA 1950
                        *********** ** *** ***** ** ***** ** ***** ******

Mouse Microutro    1951 GACCTATTGGAGACCGTTCATGTGAGAGAACAAGGGATGGTGAAGAAGCC 2000
Human Microutro    1951 GACCTTTTGGAGACTGTTCGTGTAAGAGAACAAGCAATTACAAAAAATC 2000
Canine Microutr    1951 GATCTTCTGGAGACTGTTCGCATAAGAGAGAACAAGTAACTACAAAAGGTC 2000
                        ** **  ******* ****     ** ******    * * ****    *
```

FIG. 1I

```
Mouse Microutro   2001 CAAGCAGGAACTGCCTCCTCCCCCACCAAAGAAGAGACAGATTCACG 2050
Human Microutro   2001 TAAGCAGGAACTGCCTCCTCCTCCTCCCCCAAAGAAGAGACAGATCCATG 2050
Canine Microutr   2001 TAAGCAAGAACTGCCTCCTCCTCCTCCCCCAAAGAAGAGACAGATTCCTG 2050
                       ****  ************ ***** ************** *

Mouse Microutro   2051 TGGACTTAGAGAAACTCCGAGACCTGCAGGGAGCTATGGACGACCTGGAC 2100
Human Microutro   2051 TGGATTTGGAGAAACTCAGAGACCTGCAGGGAGCTATGGATGACCTGGAC 2100
Canine Microutr   2051 TGGATCTGGAGAAGCTCAGAGACCTGCAGGGAGCCATGGATGACCTGGAT 2100
                       ****  * *****  *** ************** *****  ******

Mouse Microutro   2101 GCAGACATGAAGGAGGAGGCTGTGCGGAATGGCTGAAGCCCGTGGG 2150
Human Microutro   2101 GCTGACATGAAGGAGGAGGCAGAGTCGGAGGCGGAGGCTGTGCCGTCCGTGCGGAATGGCTGAAGCCCGTGGGG 2150
Canine Microutr   2101 GTTGACATGAAGGAGGAGGCCGGGAGCTGTGCGGAATGGCTGAAGCCCGTGTGGG 2150
                        * *  *  ***********  *   *** ** **************** ***

Mouse Microutro   2151 AGACCTGCTTATAGACTCCCTGCAGGATCACATCGAGAAAACCCTGGCGT 2200
Human Microutro   2151 AGACTTACTCATTGACTCGCTGCTGCAGGATCACATTGAAAAAATCATGGCAT 2200
Canine Microutr   2151 AGACTTACTTATCGACTTACTGCAGGATCACATTGAAAAAAACCATGGCAT 2200
                       ****  ** **  ****  * ************* ** ** **  *

Mouse Microutro   2201 TTAGAGAAGAAATTGCACCAATCAACTTAAAAGTAAAAACAATGAATGAC 2250
Human Microutro   2201 TTAGAGAAGAAATTGCACCAATCAACTTTAAAGTTAAAACGGTGAATGAT 2250
Canine Microutr   2201 TTAGAGAAGAAATTGCACCAATCAACCTAAAAGTTAAAACAGTGAATGAT 2250
                       **************************  * *****  * *  ******
```

FIG. 1J

```
Mouse Microutro   2251 CTGTCCAGTCAGCTGTCTCCACTTGACTTGCATCCATCTCTAAAGATGTC 2300
Human Microutro   2251 TTATCCAGTCAGCTGTCTCCACTTGACCTGCATCCCTCTCTAAAGATGTC 2300
Canine Microutr   2251 TTATCCAGTCAGCTGTCTCCACTTGACCTGCATCCATCTCTAAAGATGTC 2300
                       * ************* **************** ***************

Mouse Microutro   2301 TCGCCAGCTGGATGACCTTAATATGCGATGGAAACTTCTACAGTTTCCG 2350
Human Microutro   2301 TCGCCAGCTAGATGACCTTAATATGCGATGGAAACTTTACAGTTTTCTG 2350
Canine Microutr   2301 TCGCCAGCTAGATGACCTTAATATGCGATGGAAACTTCTGCAGTTTCTG 2350
                       ********* ************************** * ***** * *

Mouse Microutro   2351 TGGACGATCGCCTTAAGCAGCTCCAGGAAGCCCACAGAGATTTGGGCCA 2400
Human Microutro   2351 TGGATGATCGCCTTAAACAGCTTCAGGAAGCCCACAGAGATTTTGGACCA 2400
Canine Microutr   2351 TGGATGATCGCCTTAAACAGCTTCAGGAAGCCCATAGAGATTTTGGGCCA 2400
                       **** *********** ***** *********** ******** ** ***

Mouse Microutro   2401 TCTTCTCAACACTTTCTGTCCACTTCAGTCCAGTCCGTGCCAGCAGATC 2450
Human Microutro   2401 TCCTCTCAGCAGCATTTCTCTCCTACGTCAGTCCAGTCCGTGGCAAAGATC 2450
Canine Microutr   2401 TCCTCTCAGCAGCATTTCTTTCTACTTCAGTCCAGTCCATGGCAAAGATC 2450
                       ** ****** ** ****** ** ** ************ ** ** *****

Mouse Microutro   2451 CATTTCACATAATAAAGTGCCCTATTACATCAACCATCAAACACAGACAA 2500
Human Microutro   2451 CATTTCACATAATAAAGTGCCCTATTACATCAACCATCAAACACAGACCA 2500
Canine Microutr   2451 CATTTCACATAATAAAGTGCCCTATTACATCAACCATCAAACACAGACAA 2500
                       *********************************************** *
```

FIG. 1K

```
Mouse Microutro    2501  CCTGTTGGGATCATCCTAAAAATGACTGAGCTCTTCCAATCCCTTGCTGAT  2550
Human Microutro    2501  CCTGTTGGGACCATCCTAAAAATGACCGAACTCTTCAATCCCTTGCTGAC  2550
Canine Microutr    2501  CTTGTTGGGACCGTCCTAAAAATGACTGAACTCTTTCAATCTCTTGCTGAC  2550
                         *  ******** *  ************* *** ***** ***** *******  *

Mouse Microutro    2551  CTGAATAATGTACGTTTCTCTGCCTACCGCACAGCAATCAAAATTCGAAG   2600
Human Microutro    2551  CTGAATAATGTACGTTTTTTCTGCCTACCGTACAGCAATCAAAATCCGAAG   2600
Canine Microutr    2551  CTGAATAATGTACGTTTCTCTGCCTACCGTACAGCCATCAAAATCCGAAG   2600
                         ***************** * ********** **** ******** *****

Mouse Microutro    2601  GCTGCAAAAAGCATTATGTCTGGATCTCTTAGAGCTGAATACGACGAATG   2650
Human Microutro    2601  ACTACAAAAAGCACTATGTTTGGATCTCTTAGAGTTGAGTTGAACAAATG   2650
Canine Microutr    2601  ACTACAAAAAGCACTGTGTTTGGATCTCTTAGAGTTGAGTTGAATACAAATG   2650
                         ** * ******** * ** *  *********** *** *  ** ****

Mouse Microutro    2651  AAGTTTCAAGCAGCACACAAACTGAACCAAAATGATCAGCTCCTGAGTGTC   2700
Human Microutro    2651  AAATTTTCAAACAGCACACAAGTTGAACCAAAATGACCAGCTCCTCAGTGTT   2700
Canine Microutr    2651  AAGTTTTCAAGCAGCACACAAACTGAACCAAAATGATCAGCTTCTTAGCGTT   2700
                         ** *** ***  ********  ************* ******  **  ** **

Mouse Microutro    2701  CCAGACGTCATCAACTGTCTGACCACCACTTACGATGGGCTTGAGCAGCT   2750
Human Microutro    2701  CCAGATGTCATCATCAACTGTCTGACAACAACTTATGATGGACTTGAGCAGCAAAT   2750
Canine Microutr    2701  CCAGATGTCATCAACTGTCTGACAACAACTTATGATGGTCTTGAACAAAT   2750
                         ***** *******  **********  ** ** ** *****  ****** ***  *
```

FIG. 1L

```
Mouse Microutro   2751 GCACAAGGACTTGGTCAATGTTCCACTCTGCGTCGATATGTGTCTCAACT 2800
Human Microutro   2751 GCATAAGGACCTGGTCAACGTTCCACTCTGTGTTGATATGTGTCTCAATT 2800
Canine Microutr   2751 GCATAAGGATCTGGTCAACGTTCCACTCTGTGTGGATATGTGTCTCAACT 2800
                       *** ******* ******* ***** ***************** *** *

Mouse Microutro   2801 GGCTGCTCAACGTATACGACACGGGCCGGACTGGAAAAATTCGGGTACAG 2850
Human Microutro   2801 GGTTGCTCAATGTCTATGACACGGGTCGAACTGGAAAAATTAGAGTGCAG 2850
Canine Microutr   2801 GGTTGCTCAATGTGTATGACACGGGTCGAACTGGAAAAATAAGAGTGCAG 2850
                       ** ******* ** ** ******** ** *********** ** * ***

Mouse Microutro   2851 AGTCTGAAGATTGGATTGATGTCTCTCTCCAAAGGCCCTCTTAGAAGAGAA 2900
Human Microutro   2851 AGTCTGAAGATTGGATTGATTAATGTCTCTCTCCAAAGGTCTCTTGGAAGAAAA 2900
Canine Microutr   2851 AGTCTGAAGATTGGATTGATGTCTCTCTCCAAAGGTCTCTTAGAAGAAAA 2900
                       *************** *** ***** ************ * **** *** **

Mouse Microutro   2901 ATACAGATGTCTCTTTAAGGAGGTGGCAGGGCCAACTGAGATGTGTGACC 2950
Human Microutro   2901 ATACAGATATCTCTTTAAGGAAGTTGCGGGGCCGACAGAGAATGTGTGACC 2950
Canine Microutr   2901 ATACAGATATCTCTTTAAGGAGGTGGCAGGTCCGACAGAGAAATGTGTGACC 2950
                       ********* ** ********* ** ** ** ** ** ** ** ***** ***

Mouse Microutro   2951 AGCGGGCAGCTTGGCCTGCTACTTCACGATGCCATCCAGATCCCTAGGCAG 3000
Human Microutro   2951 AGAGGCAGCTGGCCTGGGCCTGTTACTTCATGATGCCATCCAGATCCCCGGCAG 3000
Canine Microutr   2951 AGAGGCAGCTTGGCCCTGTTACTTCATGATGCCATCCAGATCCCTCGGCAG 3000
                       ** ******* **** ** ********* *************** * ****
```

FIG. 1M

```
Mouse Microutro  3001  CTGGGGGAAGTAGCAGCCTTTGGGGGCAGTAACATTGAGCCCAGTGTCCG  3050
Human Microutro  3001  CTAGGTGAAGTAGCAGCTTTTGGGAGGCAGTAGTATTGAGCCTAGTGTTCG  3050
Canine Microutr  3001  CTGGGGGAAGTAGCAGCTTTTGGGGGCAGTAACCCAGTGTTCG  3050
                       ** ** ************ ***** ** ****** **

Mouse Microutro  3051  CAGCTGCTTCCAGCAGAATAACAACAAGCCAGAAATCAGTGTGAAGGAGT  3100
Human Microutro  3051  CAGCTGCTTCCAACAGAATAACAGATAACAAGCCAGAGAATAAGTGAAAGAGT  3100
Canine Microutr  3051  CAGCTGCTTCCAACAGAATAACAGATAACAAGCCAGAGATAAGCGTAAAAGATT  3100
                       ************ ******** ** ** ******** ** ** **

Mouse Microutro  3101  TTATAGACTGGATGCATTGGAACCCCAGTCCATGGTGTTGCCGGTT  3150
Human Microutro  3101  TTATAGATTGGATGCATTTGGAACCACAGTCCATGGTTTGGCTCCCAGTT  3150
Canine Microutr  3101  TTATAGATTGGATGCGTCTGGAACCACAGTCCATGGTCTTGGCTGCCAGTT  3150
                       ******* ******* * ******* ********** ** *** ***

Mouse Microutro  3151  CTGCATCGGGTCGCAGCTGCTGAGACTGCAAAACATCAGGCCAAATGCAA  3200
Human Microutro  3151  TTACATCGAGTGGGCAGCGGAGACTGCAAAACATCAGGCCAAATGCAA  3200
Canine Microutr  3151  TTACCCGACTGGCTGGCTGCAGACTGAGACTGCAAGCATCAAGCTAAATGCAA  3200
                        * ** ** * ** ** ** *** ****** ********

Mouse Microutro  3201  CATCTGCAAAGAATGCCCGATTGTTGGGTTCAGATACAGGAGCCTAAAGC  3250
Human Microutro  3201  CATCTGTAAAGAATGTCCAATTGTCGGGTTCAGTTCAGGTATAGAAGCCTTAAGC  3250
Canine Microutr  3201  CATCTGTAAAGAATGTCCAATAGTTGGGTTCAGGTTCAGGTATAGAAGCCTAAAGC  3250
                       ****** ******** ** ** ** ******** ******* * *****
```

FIG. 1N

```
Mouse Microutro  3251 ATTTTAATTATGATGTCTGCCAGAGTTGCTTCTTTTCTGGAAGAACAGCA 3300
Human Microutro  3251 ATTTTAACTATGATGTCTGCCAGAGTTGTTGTTCTTTTCGGGTCGAACAGCA 3300
Canine Microutr  3251 ATTTTAACTATGATGTCTGCCAGAGTTGCTTTTTTCGGGTCGAACGGCA 3300
                     ******* ** ***************** ** ** **** *** ***

Mouse Microutro  3301 AAGGGCCACAAGTTACATTACCCGATGGTAGAATACTGCATACCGACAAC 3350
Human Microutro  3301 AAAGGTCACAAATTACATTACCCAATGGTGAATATTGTATACCTACAAC 3350
Canine Microutr  3301 AAAGGTCACAAATTACATTACCCAATGGTGGAATATTGTATACCTACAAC 3350
                     ** ** ***** *********** **** ***** ***** *****

Mouse Microutro  3351 ATCTGGGAAGATGTGAGAGATTTCACTAAGGTGCTGAAGAACAAGTTCA 3400
Human Microutro  3351 ATCTGGGGAAGATGTACGAGACTTCACAAAGGTACTTAAGAACAAGTTCA 3400
Canine Microutr  3351 ATCTGGGGAAGATGTACGAGACTTCACAAAGGTGCTGAAGAATAAGTTCA 3400
                     ******* ******* ***** ***** **** ** ***** *******

Mouse Microutro  3401 GGTCCAAGAAATATTTTGCCAAACATCCTCCGGCTTGGCTACCTGCCTGTC 3450
Human Microutro  3401 GGTCGAAGAAGAAGTACTTTGCCAAACACCCCTGACTTGGTTACCTGCCTGTC 3450
Canine Microutr  3401 GATCAAAGAAATAACTTTGCCAAACATCCTCCGGCTTGGCTACCTGCCTGTC 3450
                     * ** ***** **  ********** **  ** ****** **********

Mouse Microutro  3451 CAGACCCTGCTGGAAGGGGACAACTTAGAAACTTGA 3486
Human Microutro  3451 CAGACAGTTCTTGAAGGTGACAACTTAGAGACTTGA 3486
Canine Microutr  3451 CAGACAGTACTTGAAGGTGACAACTTAGAGACTTGA 3486
                     ***** ** ******* ************ ******
```

FIG. 2A

```
Canine Microutr    1  MAKYGEHEASPDNGQNEFSDIIKSRSDEHNDVQKKTFTKWINARFSKSGK   50
Human Microutro    1  MAKYGEHEASPDNGQNEFSDIIKSRSDEHNDVQKKTFTKWINARFSKSGK   50
Mouse Microutro    1  MAKYGDLEARPDDGQNEFSDIIKSRSDEHNDVQKKTFTKWINARFSKSGK   50
                      ***** ** *  ************************************

Canine Microutr   51  PPINDMFTDLKDGRKLLDLLEGLTGTSLPKERGSTRVHALNNVNRVLQVL  100
Human Microutro   51  PPINDMFTDLKDGRKLLDLLEGLTGTSLPKERGSTRVHALNNVNRVLQVL  100
Mouse Microutro   51  PPISDMFSDLKDGRKLLDLLEGLTGTSLPKERGSTRVHALNNVNRVLQVL  100
                      *** ** ******************************************

Canine Microutr  101  HQNNVDLVNIGGTDIVDGNHKLTLGLLWSIILHWQVKDVMKDVMSDLQQT  150
Human Microutro  101  HQNNVELVNIGGTDIVDGNHKLTLGLLWSIILHWQVKDVMKDVMSDLQQT  150
Mouse Microutro  101  HQNNVDLVNIGGTDIVAGNPKLTLGLLWSIILHWQVKDVMKDIMSDLQQT  150
                      ***** ********** ** ********************* ******

Canine Microutr  151  NSEKILLSWVRQSTRPYSQVNVLNFTTSWTDGLAFNAVLHRHKPDLFSWD  200
Human Microutro  151  NSEKILLSWVRQTTRPYSQVNVLNFTTSWTDGLAFNAVLHRHKPDLFSWD  200
Mouse Microutro  151  NSEKILLSWVRQTTRPYSQVNVLNFTTSWTDGLAFNAVLHRHKPDLFDWD  200
                      ************ ********************************* **

Canine Microutr  201  RVVKMSPIERLEHAFSKAQTYLGIEKLLDPEDVAVQLPDKKSIIMYLTSL  250
Human Microutro  201  KVVKMSPIERLEHAFSKAQTYLGIEKLLDPEDVAVRLPDKKSIIMYLTSL  250
Mouse Microutro  201  EMVKMSPIERLDHAFDKAHTSLGIEKLLSPETVAVHLPDKKSIIMYLTSL  250
                       ********* *** ** * ******  * *** ************
```

FIG. 2B

```
Canine Microutr    251 FEVLPQQVTLDAIREVETLPRKYKKECEEGEISIQSSAPEEEHECPGAET 300
Human Microutro    251 FEVLPQQVTIDAIREVETLPRKYKKECEEEAINIQSTAPEEEHESPRAET 300
Mouse Microutro    251 FEVLPQQVTIDAIREVETLPRKYKKECEEEIHIQSAVLAEEGQSPRAET 300
                       ********.*********************  .* .. ** ***

Canine Microutr    301 PSTVTEVDTDLDSYQIALEEVLTWLLSAEDTFQEQDDISDDVEEVKEQFT 350
Human Microutro    301 PSTVTEVDMDLDSYQIALEEVLTWLLSAEDTFQEQDDISDDVEEVKDQFA 350
Mouse Microutro    301 PSTVTEVDMDLDSYQIALEEVLTWLLSAEDTFQEQHDISDDVEEVKEQFA 350
                       ******** ************************* *********.*.

Canine Microutr    351 THEAFMMELTAHQSSVGSVLQAGNQLITQGTLSDEEEFEIQEQMTLLNAR 400
Human Microutro    351 THEAFMMELTAHQSSVGSVLQAGNQLITQGTLSDEEEFEIQEQMTLLNAR 400
Mouse Microutro    351 THETFMMELTAHQSSVGSVLQAGNQLMTQGTLSREEEFEIQEQMTLLNAR 400
                       ***.*********************.******.***************

Canine Microutr    401 WEALRVDSMNRQSRLHDVLMELQKKQLQQLSAWLTLTEERIQKMETCPLD 450
Human Microutro    401 WEALRVESMDRQSRLHDVLMELQKKQLQQLSAWLTLTEERIQKMETCPLD 450
Mouse Microutro    401 WEALRVESMERQSRLHDALMELQKKQLQQLSSWLALTEERIQKMESLPLG 450
                       ******.**.*******.************.**.**********. **

Canine Microutr    451 DDLKSLQKLLEDHKRLQNDLEAEQVKVNSLTHMVVIVDENSGESATAVLE 500
Human Microutro    451 DDVKSLQKLLEEHKSLQSDLEAEQVKVNSLTHMVVIVDENSGESATAILE 500
Mouse Microutro    451 DDLPSLQKLLQEHKSLQNDLEAEQVKVNSLTHMVVIVDENSGESATALLE 500
                       **  ******.:**.**.*************************** **

Canine Microutr    501 DQLQKLGERWTAVCRWTEERWSRLQEINILWQELLEEQCLLKAWLTEKEE 550
Human Microutro    501 DQLQKLGERWTAVCRWTEERWNRLQEINILWQELLEEQCLLKAWLTEKEE 550
Mouse Microutro    501 DQLQKLGERWTAVCRWTEERWNRLQEISILWQELLEEQCLLEAWLTEKEE 550
                       ********************* ******.************.*******
```

FIG. 2C

```
Canine Microutr  551 ALNKVQTSNFKDQKELSVSIRRLAILKEDMEMKRQALDQLSEIGQDVGQL 600
Human Microutro  551 ALNKVQTSNFKDQKELSVSVRRLAILKEDMEMKRQTLDQLSEIGQDVGQL 600
Mouse Microutro  551 ALDKVQTSNFKDQKELSVSVRRLAILKEDMEMKRQTLDQLSEIGQDVGQL 600
                     ** .*********************.***********************

Canine Microutr  601 VDNPKASKKINSDSEELTQRWDSLVQRLEDSSSQVTQAVAKLGMSQIPQK 650
Human Microutro  601 LDNSKASKKINSDSEELTQRWDSLVQRLEDSSNQVTQAVAKLGMSQIPQK 650
Mouse Microutro  601 LSNPKASKKMNSDSEELTQRWDSLVQRLEDSSNQVTQAVAKLGMSQIPQK 650
                      .* ********:*******************:****************

Canine Microutr  651 DLLETVRIREQVTTKRSKQELPPPPPKKRQIPVDLEKLRDLQGAMDDLD 700
Human Microutro  651 DLLETVRVREQAITKKKSKQELPPPPPPKKRQIHVDLEKLRDLQGAMDDLD 700
Mouse Microutro  651 DLLETVHVREQGMVKKPKQELPPPPPPKKRQIHVDLEKLRDLQGAMDDLD 700
                     ******..*** .***  *. ********.* ****************

Canine Microutr  701 VDMKEAEAVRNGWKPVGDLLIDSLQDHIEKTMAFREEIAPINLKVKTVND 750
Human Microutro  701 ADMKEAESVRNGWKPVGDLLIDSLQDHIEKIMAFREEIAPINFKVKTVND 750
Mouse Microutro  701 ADMKEVEAVRNGWKPVGDLLIDSLQDHIEKTLAFREEIAPINLKVKTMND 750
                      **** .**********************. ***********:****:**

Canine Microutr  751 LSSQLSPLDLHPSLKMSRQLDDLNMRWKLLQVSVDDRLKQLQEAHRDFGP 800
Human Microutro  751 LSSQLSPLDLHPSLKMSRQLDDLNMRWKLLQVSVDDRLKQLQEAHRDFGP 800
Mouse Microutro  751 LSSQLSPLDLHPSLKMSRQLDDLNMRWKLLQVSVDDRLKQLQEAHRDFGP 800
                     **************************************************
```

FIG. 2D

```
Canine Microutr   801  SSQHFLSTSVQLPWQRSISHNKVPYYINHQTQTTCWDRPKMTELFQSLAD  850
Human Microutro   801  SSQHFLSTSVQLPWQRSISHNKVPYYINHQTQTTCWDHPKMTELFQSLAD  850
Mouse Microutro   801  SSQHFLSTSVQLPWQRSISHNKVPYYINHQTQTTCWDHPKMTELFQSLAD  850
                       *********************************** ************

Canine Microutr   851  LNNVRFSAYRTAIKIRRLQKALCLDLLELNTTNEVFKQHKLNQNDQLLSV  900
Human Microutro   851  LNNVRFSAYRTAIKIRRLQKALCLDLLELSTTNEIFKQHKLNQNDQLLSV  900
Mouse Microutro   851  LNNVRFSAYRTAIKIRRLQKALCLDLLELNTTNEVFKQHKLNQNDQLLSV  900
                       ***************************** **** *************

Canine Microutr   901  PDVINCLTTTYDGLEQMHKDLVNVPLCVDMCLNWLLNVYDTGRTGKIRVQ  950
Human Microutro   901  PDVINCLTTTYDGLEQMHKDLVNVPLCVDMCLNWLLNVYDTGRTGKIRVQ  950
Mouse Microutro   901  PDVINCLTTTYDGLEQLHKDLVNVPLCVDMCLNWLLNVYDTGRTGKIRVQ  950
                       **************** ********************************

Canine Microutr   951  SLKIGLMSLSKGLLEEKYRYLFKEVAGPTEMCDQRQLGLLLHDAIQIPRQ  1000
Human Microutro   951  SLKIGLMSLSKGLLEEKYRYLFKEVAGPTEMCDQRQLGLLLHDAIQIPRQ  1000
Mouse Microutro   951  SLKIGLMSLSKGLLEEKYRCLFKEVAGPTEMCDQRQLGLLLHDAIQIPRQ  1000
                       ******************* *****************************

Canine Microutr  1001  LGEVAAFGGSNIEPSVRSCFQQNNNKPEISVKDEFIDWMRLEPQSMVWLPV  1050
Human Microutro  1001  LGEVAAFGGSNIEPSVRSCFQQNNNKPEISVKEFIDWMHLEPQSMVWLPV  1050
Mouse Microutro  1001  LGEVAAFGGSNIEPSVRSCFQQNNNKPEISVKEFIDWMHLEPQSMVWLPV  1050
                       ******************************** ***** **********

Canine Microutr  1051  LHRVAAAETAKHQAKCNICKECPIVGFRYRSLKHFNYDVCQSCFFSGRTA  1100
Human Microutro  1051  LHRVAAAETAKHQAKCNICKECPIVGFRYRSLKHFNYDVCQSCFFSGRTA  1100
Mouse Microutro  1051  LHRVAAAETAKHQAKCNICKECPIVGFRYRSLKHFNYDVCQSCFFSGRTA  1100
                       **************************************************
```

FIG. 2E

```
Canine Microutr  1101  KGHKLHYPMVEYCIPTTSGEDVRDFTKVLKNKFRSKKYFAKHPRLGYLPV  1150
Human Microutro  1101  KGHKLHYPMVEYCIPTTSGEDVRDFTKVLKNKFRSKKYFAKHPRLGYLPV  1150
Mouse Microutro  1101  KGHKLHYPMVEYCIPTTSGEDVRDFTKVLKNKFRSKKYFAKHPRLGYLPV  1150
                      **************************************************

Canine Microutr  1151  QTVLEGDNLETN  1162
Human Microutro  1151  QTVLEGDNLETN  1162
Mouse Microutro  1151  QTVLEGDNLETN  1162
                      ************
```

FIG 3K

SEQUENCE LISTING

<160> NUMBER OF SEQ ID NOS: 12

<210> SEQ ID NO 1
<211> LENGTH: 3507
<212> TYPE: DNA
<213> ORGANISM: Artificial
<220> FEATURE:
<223> OTHER INFORMATION: canine microutrophin

<400> SEQUENCE: 1

```
atcgatccac catggccaag tatggagaac atgaagccag tcctgataat gggcagaacg      60
aattcagtga catcattaag tccagatctg atgaacacaa tgacgtgcag aagaaaacct     120
ttaccaaatg gatcaatgcg cgattttcaa agagtggaaa accacccatc aatgatatgt     180
tcacagacct caaagatgga aggaagctcc tggatcttct ggaaggcctc acaggaacat     240
cactgccaaa ggaacgtggt tccacaaggg tacatgcttt aaataatgtc aacagagtgc     300
tgcaggtttt gcatcagaat aatgtggatt tagtgaatat aggaggaact gacattgtag     360
atggaaatca caaactgact ttgggattac tttggagcat cattttgcac tggcaggtaa     420
aagatgtcat gaaagatgtc atgtcagacc tgcagcagac aaacagtgag aagatcctac     480
tgagctgggt gcgccagtct actaggccgt acagccaggt caacgtcctc aacttcacca     540
ccagctggac agatggactg gcctttaatg ctgtgctgca ccgacataaa cctgatctct     600
tcagctggga tagagttgtc aaaatgtccc caattgagag acttgaacat gccttcagca     660
aagctcaaac ttatttggga attgaaaagc tgttagatcc tgaagatgtt gccgttcaac     720
ttcctgacaa gaaatccata attatgtatt taacatcttt gtttgaggtg cttcctcagc     780
aagtcactct agatgccatc cgtgaagtag agacactccc aaggaaatat aagaaagaat     840
gtgaagaagg agagattagt atacagagct cagcgccaga ggaggagcat gagtgtcccg     900
gagctgaaac ccccagcact gtcactgaag ttgacacgga tctggacagc tatcagatag     960
cactggagga agtgctgacc tggttgcttt ctgccgagga cactttccag gagcaggatg    1020
acatttctga tgatgtagaa gaagtcaaag agcagtttac tacccatgaa gcttttatga    1080
tggagctgac agcgcaccag agcagtgtgg gcagtgtcct gcaggcagga aaccagctga    1140
taacgcaagg aactctgtca gatgaggagg aatttgaaat tcaggaacaa atgaccctgc    1200
taaatgctag atgggaggca ctcagggtgg atagtatgaa cagacagtcc cggctgcatg    1260
atgtgttgat ggaactacaa aagaagcagt tgcaacagct ctctgcctgg ttaacactca    1320
cagaagaacg cattcagaag atggaaacct gccccctgga tgatgattta aaatccctac    1380
aaaagctact agaagatcat aaacgtttgc aaaatgatct tgaggcggaa caggtgaagg    1440
taaattcact aacacacatg gtggtgattg ttgatgaaaa cagtggtgag agtgccactg    1500
ctgttctgga agatcagtta cagaaacttg gtgaacgctg gacagcagtg tgccgttgga    1560
```

-continued

```
cagaggaacg ttggagtagg ctacaagaaa ttaatatatt gtggcaggaa ttattagaag    1620
aacagtgctt gttgaaagct tggctaactg aaaaagaaga ggccttaaat aaagtccaga    1680
cgagcaactt caaagaccaa aaggaactaa gtgtcagcat ccgacgattg gctattttga    1740
aggaagacat ggaaatgaaa cgtcaggcat tggatcagct aagtgagatt ggccaggatg    1800
tgggtcaatt agttgataat cccaaggcat ctaagaagat caacagtgac tcagaggaac    1860
taactcagag atgggattct ttggttcaga gactagaaga ttcctctaac caggtgactc    1920
aggctgtggc aaagctgggg atgtcccaaa ttcctcagaa agatcttctg gagactgttc    1980
gcataagaga acaagtaact acaaaaaggt ctaagcaaga actgcctcct cctcctcccc    2040
caaagaagag acagattcct gtcgacctgg agaagctcag agacctgcag ggagccatgg    2100
atgacctgga tgttgacatg aaggaggcgg aggctgtgag aatggctgg aagcctgtgg     2160 gagacttact tatcgactca ctgcaggatc acattgaaaa aaccatggca tttagagaag    2220
aaattgcacc aatcaaccta aaagttaaaa cagtgaatga tttatccagt cagctgtctc    2280
cacttgacct gcatccatct ctaaagatgt ctcgccagct agatgacctt aatatgcgat    2340
ggaaacttct gcaggtttct gtggatgatc gccttaaaca gcttcaggaa gcccatagag    2400
attttgggcc atcctctcag cattttcttt ctacttcagt ccagctgcca tgcaaagat    2460 ccatttcaca taataaagtg ccctattaca tcaaccatca aacacagaca acttgttggg    2520
accgtcctaa aatgactgaa ctctttcaat ctcttgctga cctgaataat gtacgtttct    2580
ctgcctaccg tacagccatc aaaatccgaa gactacaaaa agcactgtgt ttggatctct    2640
tagagttgaa tacaacaaat gaagttttca agcagcacaa actgaaccaa atgatcagc    2700 ttcttagcgt tccagatgtc atcaactgtc tgacaacaac ttatgatggt cttgaacaaa    2760
tgcataagga tctggtcaac gttccactct gtgtggatat gtgtctcaac tggttgctca    2820
atgtgtatga cacgggtcga actggaaaaa taagagtgca gagtctgaag attggattga    2880
tgtctctctc caaaggtctc ttagaagaaa aatacagata tctctttaag gaggtggcag    2940
gtccgacaga aatgtgtgac cagaggcagc ttggcctgtt acttcatgat gccatccaga    3000
tccctcggca gctggggaa gtagcagctt ttgggggcag taatattgaa cccagtgttc     3060
gcagctgctt ccaacagaat aacaataagc cagagataag cgtaaaagat tttatagatt    3120
ggatgcgtct ggaaccacag tccatggttt ggctgccagt tttacaccga gtggctgcag    3180
ctgagactgc aaagcatcaa gctaaatgca acatctgtaa agaatgtcca atagttgggt    3240
tcaggtatag aagcctaaag catttttaact atgatgtctg ccagagttgc tttttttcgg    3300
gtcgaacggc aaaaggtcac aaattacatt acccaatggt ggaatattgt atacctacaa    3360
catctgggga agatgtacga gacttcacaa aggtgctgaa gaataagttc agatcaaaga    3420
aatactttgc caaacatcct cggcttggct acctgcctgt ccagacagta cttgaaggtg    3480
acaacttaga gacttgaaaa actcgag                                          3507
```

<210> SEQ ID NO 2
<211> LENGTH: 1162
<212> TYPE: PRT
<213> ORGANISM: Artificial
<220> FEATURE:
<223> OTHER INFORMATION: Canine Microutrophin

<400> SEQUENCE: 2

```
Met Ala Lys Tyr Gly Glu His Glu Ala Ser Pro Asp Asn Gly Gln Asn
1               5                   10                  15
```

-continued

Glu Phe Ser Asp Ile Ile Lys Ser Arg Ser Asp Glu His Asn Asp Val
            20                  25                  30

Gln Lys Lys Thr Phe Thr Lys Trp Ile Asn Ala Arg Phe Ser Lys Ser
        35                  40                  45

Gly Lys Pro Pro Ile Asn Asp Met Phe Thr Asp Leu Lys Asp Gly Arg
    50                  55                  60

Lys Leu Leu Asp Leu Leu Glu Gly Leu Thr Gly Thr Ser Leu Pro Lys
65                  70                  75                  80

Glu Arg Gly Ser Thr Arg Val His Ala Leu Asn Asn Val Asn Arg Val
                85                  90                  95

Leu Gln Val Leu His Gln Asn Val Asp Leu Val Asn Ile Gly Gly
            100                 105                 110

Thr Asp Ile Val Asp Gly Asn His Lys Leu Thr Leu Gly Leu Leu Trp
            115                 120                 125

Ser Ile Ile Leu His Trp Gln Val Lys Asp Val Met Lys Asp Val Met
            130                 135                 140

Ser Asp Leu Gln Gln Thr Asn Ser Glu Lys Ile Leu Leu Ser Trp Val
145                 150                 155                 160

Arg Gln Ser Thr Arg Pro Tyr Ser Gln Val Asn Val Leu Asn Phe Thr
                165                 170                 175

Thr Ser Trp Thr Asp Gly Leu Ala Phe Asn Ala Val Leu His Arg His
            180                 185                 190

Lys Pro Asp Leu Phe Ser Trp Asp Arg Val Val Lys Met Ser Pro Ile
            195                 200                 205

Glu Arg Leu Glu His Ala Phe Ser Lys Ala Gln Thr Tyr Leu Gly Ile
            210                 215                 220

Glu Lys Leu Leu Asp Pro Glu Asp Val Ala Val Gln Leu Pro Asp Lys
225                 230                 235                 240

Lys Ser Ile Ile Met Tyr Leu Thr Ser Leu Phe Glu Val Leu Pro Gln
            245                 250                 255

Gln Val Thr Leu Asp Ala Ile Arg Glu Val Glu Thr Leu Pro Arg Lys
            260                 265                 270

Tyr Lys Lys Glu Cys Glu Glu Gly Glu Ile Ser Ile Gln Ser Ser Ala
            275                 280                 285

Pro Glu Glu Glu His Glu Cys Pro Gly Ala Glu Thr Pro Ser Thr Val
            290                 295                 300

Thr Glu Val Asp Thr Asp Leu Asp Ser Tyr Gln Ile Ala Leu Glu Glu
305                 310                 315                 320

Val Leu Thr Trp Leu Leu Ser Ala Glu Asp Thr Phe Gln Glu Gln Asp
            325                 330                 335

Asp Ile Ser Asp Asp Val Glu Val Lys Glu Gln Phe Thr Thr His
            340                 345                 350

Glu Ala Phe Met Met Glu Leu Thr Ala His Gln Ser Ser Val Gly Ser
            355                 360                 365

Val Leu Gln Ala Gly Asn Gln Leu Ile Thr Gln Gly Thr Leu Ser Asp
            370                 375                 380

Glu Glu Glu Phe Glu Ile Gln Glu Gln Met Thr Leu Leu Asn Ala Arg
385                 390                 395                 400

Trp Glu Ala Leu Arg Val Asp Ser Met Asn Arg Gln Ser Arg Leu His
                405                 410                 415

Asp Val Leu Met Glu Leu Gln Lys Lys Gln Leu Gln Gln Leu Ser Ala
            420                 425                 430

-continued

```
Trp Leu Thr Leu Thr Glu Glu Arg Ile Gln Lys Met Glu Thr Cys Pro
            435                 440                 445

Leu Asp Asp Asp Leu Lys Ser Leu Gln Lys Leu Leu Glu Asp His Lys
        450                 455                 460

Arg Leu Gln Asn Asp Leu Glu Ala Glu Gln Val Lys Val Asn Ser Leu
465                 470                 475                 480

Thr His Met Val Val Ile Val Asp Glu Asn Ser Gly Glu Ser Ala Thr
                485                 490                 495

Ala Val Leu Glu Asp Gln Leu Gln Lys Leu Gly Glu Arg Trp Thr Ala
            500                 505                 510

Val Cys Arg Trp Thr Glu Glu Arg Trp Ser Arg Leu Gln Glu Ile Asn
            515                 520                 525

Ile Leu Trp Gln Glu Leu Leu Glu Glu Gln Cys Leu Leu Lys Ala Trp
        530                 535                 540

Leu Thr Glu Lys Glu Glu Ala Leu Asn Lys Val Gln Thr Ser Asn Phe
545                 550                 555                 560

Lys Asp Gln Lys Glu Leu Ser Val Ser Ile Arg Arg Leu Ala Ile Leu
                565                 570                 575

Lys Glu Asp Met Glu Met Lys Arg Gln Ala Leu Asp Gln Leu Ser Glu
            580                 585                 590

Ile Gly Gln Asp Val Gly Gln Leu Val Asp Asn Pro Lys Ala Ser Lys
        595                 600                 605

Lys Ile Asn Ser Asp Ser Glu Glu Leu Thr Gln Arg Trp Asp Ser Leu
610                 615                 620

Val Gln Arg Leu Glu Asp Ser Ser Asn Gln Val Thr Gln Ala Val Ala
625                 630                 635                 640

Lys Leu Gly Met Ser Gln Ile Pro Gln Lys Asp Leu Leu Glu Thr Val
                645                 650                 655

Arg Ile Arg Glu Gln Val Thr Thr Lys Arg Ser Lys Gln Glu Leu Pro
            660                 665                 670

Pro Pro Pro Pro Lys Lys Arg Gln Ile Pro Val Asp Leu Glu Lys
        675                 680                 685

Leu Arg Asp Leu Gln Gly Ala Met Asp Asp Leu Asp Val Asp Met Lys
        690                 695                 700

Glu Ala Glu Ala Val Arg Asn Gly Trp Lys Pro Val Gly Asp Leu Leu
705                 710                 715                 720

Ile Asp Ser Leu Gln Asp His Ile Glu Lys Thr Met Ala Phe Arg Glu
                725                 730                 735

Glu Ile Ala Pro Ile Asn Leu Lys Val Lys Thr Val Asn Asp Leu Ser
            740                 745                 750

Ser Gln Leu Ser Pro Leu Asp Leu His Pro Ser Leu Lys Met Ser Arg
        755                 760                 765

Gln Leu Asp Asp Leu Asn Met Arg Trp Lys Leu Leu Gln Val Ser Val
        770                 775                 780

Asp Asp Arg Leu Lys Gln Leu Gln Glu Ala His Arg Asp Phe Gly Pro
785                 790                 795                 800

Ser Ser Gln His Phe Leu Ser Thr Ser Val Gln Leu Pro Trp Gln Arg
                805                 810                 815

Ser Ile Ser His Asn Lys Val Pro Tyr Tyr Ile Asn His Gln Thr Gln
            820                 825                 830

Thr Thr Cys Trp Asp Arg Pro Lys Met Thr Glu Leu Phe Gln Ser Leu
        835                 840                 845

Ala Asp Leu Asn Asn Val Arg Phe Ser Ala Tyr Arg Thr Ala Ile Lys
```

-continued 850                 855                 860
Ile Arg Arg Leu Gln Lys Ala Leu Cys Leu Asp Leu Leu Glu Leu Asn
865                 870                 875                 880

Thr Thr Asn Glu Val Phe Lys Gln His Lys Leu Asn Gln Asn Asp Gln
                885                 890                 895

Leu Leu Ser Val Pro Asp Val Ile Asn Cys Leu Thr Thr Thr Tyr Asp
                900                 905                 910

Gly Leu Glu Gln Met His Lys Asp Leu Val Asn Val Pro Leu Cys Val
                915                 920                 925

Asp Met Cys Leu Asn Trp Leu Leu Asn Val Tyr Asp Thr Gly Arg Thr
930                 935                 940

Gly Lys Ile Arg Val Gln Ser Leu Lys Ile Gly Leu Met Ser Leu Ser
945                 950                 955                 960

Lys Gly Leu Leu Glu Glu Lys Tyr Arg Tyr Leu Phe Lys Glu Val Ala
                965                 970                 975

Gly Pro Thr Glu Met Cys Asp Gln Arg Gln Leu Gly Leu Leu Leu His
                980                 985                 990

Asp Ala Ile Gln Ile Pro Arg Gln Leu Gly Glu Val Ala Ala Phe Gly
                995                 1000                1005

Gly Ser Asn Ile Glu Pro Ser Val Arg Ser Cys Phe Gln Gln Asn
        1010                1015                1020

Asn Asn Lys Pro Glu Ile Ser Val Lys Asp Phe Ile Asp Trp Met
        1025                1030                1035

Arg Leu Glu Pro Gln Ser Met Val Trp Leu Pro Val Leu His Arg
        1040                1045                1050

Val Ala Ala Glu Thr Ala Lys His Gln Ala Lys Cys Asn Ile
        1055                1060                1065

Cys Lys Glu Cys Pro Ile Val Gly Phe Arg Tyr Arg Ser Leu Lys
        1070                1075                1080

His Phe Asn Tyr Asp Val Cys Gln Ser Cys Phe Phe Ser Gly Arg
        1085                1090                1095

Thr Ala Lys Gly His Lys Leu His Tyr Pro Met Val Glu Tyr Cys
        1100                1105                1110

Ile Pro Thr Thr Ser Gly Glu Asp Val Arg Asp Phe Thr Lys Val
        1115                1120                1125

Leu Lys Asn Lys Phe Arg Ser Lys Lys Tyr Phe Ala Lys His Pro
        1130                1135                1140

Arg Leu Gly Tyr Leu Pro Val Gln Thr Val Leu Glu Gly Asp Asn
        1145                1150                1155

Leu Glu Thr Asn
        1160

<210> SEQ ID NO 3
<211> LENGTH: 988
<212> TYPE: PRT
<213> ORGANISM: Human Utrophin

<400> SEQUENCE: 3

Met Gln Ile Leu Arg Cys Leu Gln Lys Cys Gly Lys Leu Lys Met Met
1                   5                   10                  15

Ala Val Val Arg Thr Ser Leu Gln Lys Val Val Leu Leu His Arg
                20                  25                  30

Leu Gln Arg Met Ala Val Ser Ser Pro Arg Tyr Gln Lys Leu Cys Lys
            35                  40                  45

-continued

```
Asp Ile Gln Ala Glu Ile Asp Ala His Asn Asp Ile Phe Lys Ser Ile
 50                  55                  60

Asp Gly Asn Arg Gln Lys Met Val Lys Ala Leu Gly Asn Ser Glu Glu
 65                  70                  75                  80

Ala Thr Met Leu Gln His Arg Leu Asp Asp Met Asn Gln Arg Trp Asn
                 85                  90                  95

Asp Leu Lys Ala Lys Ser Ala Ser Ile Arg Ala His Leu Glu Ala Ser
            100                 105                 110

Ala Glu Lys Trp Asn Arg Leu Leu Met Ser Leu Glu Glu Leu Ile Lys
        115                 120                 125

Trp Leu Asn Met Lys Asp Glu Glu Leu Lys Lys Gln Met Pro Ile Gly
    130                 135                 140

Gly Asp Val Pro Ala Leu Gln Leu Gln Tyr Asp His Cys Lys Ala Leu
145                 150                 155                 160

Arg Arg Glu Leu Lys Glu Lys Glu Tyr Ser Val Leu Asn Ala Val Asp
                165                 170                 175

Gln Ala Arg Val Phe Leu Ala Asp Gln Pro Ile Glu Ala Pro Glu Glu
            180                 185                 190

Pro Arg Arg Asn Leu Gln Ser Lys Thr Glu Leu Thr Pro Glu Glu Arg
        195                 200                 205

Ala Gln Lys Ile Ala Lys Ala Met Arg Lys Gln Ser Ser Glu Val Lys
    210                 215                 220

Glu Lys Trp Glu Ser Leu Asn Ala Val Thr Ser Asn Trp Gln Lys Gln
225                 230                 235                 240

Val Asp Lys Ala Leu Glu Lys Leu Arg Asp Leu Gln Gly Ala Met Asp
                245                 250                 255

Asp Leu Asp Ala Asp Met Lys Glu Ala Glu Ser Val Arg Asn Gly Trp
            260                 265                 270

Lys Pro Val Gly Asp Leu Leu Ile Asp Ser Leu Gln Asp His Ile Glu
        275                 280                 285

Lys Ile Met Ala Phe Arg Glu Glu Ile Ala Pro Ile Asn Phe Lys Val
    290                 295                 300

Lys Thr Val Asn Asp Leu Ser Ser Gln Leu Ser Pro Leu Asp Leu His
305                 310                 315                 320

Pro Ser Leu Lys Met Ser Arg Gln Leu Asp Asp Leu Asn Met Arg Trp
                325                 330                 335

Lys Leu Leu Gln Val Ser Val Asp Asp Arg Leu Lys Gln Leu Gln Glu
            340                 345                 350

Ala His Arg Asp Phe Gly Pro Ser Gln His Phe Leu Ser Thr Ser
        355                 360                 365

Val Gln Leu Pro Trp Gln Arg Ser Ile Ser His Asn Lys Val Pro Tyr
    370                 375                 380

Tyr Ile Asn His Gln Thr Gln Thr Thr Cys Trp Asp His Pro Lys Met
385                 390                 395                 400

Thr Glu Leu Phe Gln Ser Leu Ala Asp Leu Asn Asn Val Arg Phe Ser
                405                 410                 415

Ala Tyr Arg Thr Ala Ile Lys Ile Arg Arg Leu Gln Lys Ala Leu Cys
            420                 425                 430

Leu Asp Leu Leu Glu Leu Ser Thr Thr Asn Glu Ile Phe Lys Gln His
        435                 440                 445

Lys Leu Asn Gln Asn Asp Gln Leu Leu Ser Val Pro Asp Val Ile Asn
    450                 455                 460

Cys Leu Thr Thr Thr Tyr Asp Gly Leu Glu Gln Met His Lys Asp Leu
```

```
                465                 470                 475                 480
Val Asn Val Pro Leu Cys Val Asp Met Cys Leu Asn Trp Leu Leu Asn
                    485                 490                 495

Val Tyr Asp Thr Gly Arg Thr Gly Lys Ile Arg Val Gln Ser Leu Lys
            500                 505                 510

Ile Gly Leu Met Ser Leu Ser Lys Gly Leu Leu Glu Glu Lys Tyr Arg
                515                 520                 525

Tyr Leu Phe Lys Glu Val Ala Gly Pro Thr Glu Met Cys Asp Gln Arg
            530                 535                 540

Gln Leu Gly Leu Leu His Asp Ala Ile Gln Ile Pro Arg Gln Leu
545                 550                 555                 560

Gly Glu Val Ala Ala Phe Gly Gly Ser Asn Ile Glu Pro Ser Val Arg
                    565                 570                 575

Ser Cys Phe Gln Gln Asn Asn Asn Lys Pro Glu Ile Ser Val Lys Glu
                580                 585                 590

Phe Ile Asp Trp Met His Leu Glu Pro Gln Ser Met Val Trp Leu Pro
            595                 600                 605

Val Leu His Arg Val Ala Ala Ala Glu Thr Ala Lys His Gln Ala Lys
        610                 615                 620

Cys Asn Ile Cys Lys Glu Cys Pro Ile Val Gly Phe Arg Tyr Arg Ser
625                 630                 635                 640

Leu Lys His Phe Asn Tyr Asp Val Cys Gln Ser Cys Phe Phe Ser Gly
                    645                 650                 655

Arg Thr Ala Lys Gly His Lys Leu His Tyr Pro Met Val Glu Tyr Cys
                660                 665                 670

Ile Pro Thr Thr Ser Gly Glu Asp Val Arg Asp Phe Thr Lys Val Leu
            675                 680                 685

Lys Asn Lys Phe Arg Ser Lys Lys Tyr Phe Ala Lys His Pro Arg Leu
        690                 695                 700

Gly Tyr Leu Pro Val Gln Thr Val Leu Glu Gly Asp Asn Leu Glu Thr
705                 710                 715                 720

Pro Ile Thr Leu Ile Ser Met Trp Pro Glu His Tyr Asp Pro Ser Gln
                    725                 730                 735

Ser Pro Gln Leu Phe His Asp Asp Thr His Ser Arg Ile Glu Gln Tyr
                740                 745                 750

Ala Thr Arg Leu Ala Gln Met Glu Arg Thr Asn Gly Ser Phe Leu Thr
            755                 760                 765

Asp Ser Ser Ser Thr Thr Gly Ser Val Glu Asp His Ala Leu Ile
        770                 775                 780

Gln Gln Tyr Cys Gln Thr Leu Gly Gly Glu Ser Pro Val Ser Gln Pro
785                 790                 795                 800

Gln Ser Pro Ala Gln Ile Leu Lys Ser Val Glu Arg Glu Arg Gly
                    805                 810                 815

Glu Leu Glu Arg Ile Ile Ala Asp Leu Glu Glu Gln Arg Asn Leu
                820                 825                 830

Gln Val Glu Tyr Glu Gln Leu Lys Asp Gln His Leu Arg Arg Gly Leu
            835                 840                 845

Pro Val Gly Ser Pro Glu Ser Ile Ile Ser Pro His His Thr Ser
850                 855                 860

Glu Asp Ser Glu Leu Ile Ala Glu Ala Lys Leu Leu Arg Gln His Lys
865                 870                 875                 880

Gly Arg Leu Glu Ala Arg Met Gln Ile Leu Glu Asp His Asn Lys Gln
                    885                 890                 895
```

```
Leu Glu Ser Gln Leu His Arg Leu Arg Gln Leu Leu Glu Gln Pro Glu
                900                 905                 910
Ser Asp Ser Arg Ile Asn Gly Val Ser Pro Trp Ala Ser Pro Gln His
            915                 920                 925
Ser Ala Leu Ser Tyr Ser Leu Asp Pro Asp Ala Ser Gly Pro Gln Phe
        930                 935                 940
His Gln Ala Ala Gly Glu Asp Leu Leu Ala Pro Pro His Asp Thr Ser
945                 950                 955                 960
Thr Asp Leu Thr Glu Val Met Glu Gln Ile His Ser Thr Phe Pro Ser
                965                 970                 975
Cys Cys Pro Asn Val Pro Ser Arg Pro Gln Ala Met
                980                 985

<210> SEQ ID NO 4
<211> LENGTH: 1162
<212> TYPE: PRT
<213> ORGANISM: artificial
<220> FEATURE:
<223> OTHER INFORMATION: human microutrophin

<400> SEQUENCE: 4

Met Ala Lys Tyr Gly Glu His Glu Ala Ser Pro Asp Asn Gly Gln Asn
1               5                   10                  15
Glu Phe Ser Asp Ile Ile Lys Ser Arg Ser Asp Glu His Asn Asp Val
            20                  25                  30
Gln Lys Lys Thr Phe Thr Lys Trp Ile Asn Ala Arg Phe Ser Lys Ser
        35                  40                  45
Gly Lys Pro Pro Ile Asn Asp Met Phe Thr Asp Leu Lys Asp Gly Arg
    50                  55                  60
Lys Leu Leu Asp Leu Leu Glu Gly Leu Thr Gly Thr Ser Leu Pro Lys
65                  70                  75                  80
Glu Arg Gly Ser Thr Arg Val His Ala Leu Asn Asn Val Asn Arg Val
                85                  90                  95
Leu Gln Val Leu His Gln Asn Asn Val Glu Leu Val Asn Ile Gly Gly
            100                 105                 110
Thr Asp Ile Val Asp Gly Asn His Lys Leu Thr Leu Gly Leu Leu Trp
        115                 120                 125
Ser Ile Ile Leu His Trp Gln Val Lys Asp Val Met Lys Asp Val Met
    130                 135                 140
Ser Asp Leu Gln Gln Thr Asn Ser Glu Lys Ile Leu Leu Ser Trp Val
145                 150                 155                 160
Arg Gln Thr Thr Arg Pro Tyr Ser Gln Val Asn Val Leu Asn Phe Thr
                165                 170                 175
Thr Ser Trp Thr Asp Gly Leu Ala Phe Asn Ala Val Leu His Arg His
            180                 185                 190
Lys Pro Asp Leu Phe Ser Trp Asp Lys Val Val Lys Met Ser Pro Ile
        195                 200                 205
Glu Arg Leu Glu His Ala Phe Ser Lys Ala Gln Thr Tyr Leu Gly Ile
    210                 215                 220
Glu Lys Leu Leu Asp Pro Glu Asp Val Ala Val Arg Leu Pro Asp Lys
225                 230                 235                 240
Lys Ser Ile Ile Met Tyr Leu Thr Ser Leu Phe Glu Val Leu Pro Gln
                245                 250                 255
Gln Val Thr Ile Asp Ala Ile Arg Glu Val Glu Thr Leu Pro Arg Lys
            260                 265                 270
```

-continued

```
Tyr Lys Lys Glu Cys Glu Glu Ala Ile Asn Ile Gln Ser Thr Ala
            275                 280                 285
Pro Glu Glu His Glu Ser Pro Arg Ala Glu Thr Pro Ser Thr Val
    290                 295                 300
Thr Glu Val Asp Met Asp Leu Asp Ser Tyr Gln Ile Ala Leu Glu Glu
305                 310                 315                 320
Val Leu Thr Trp Leu Leu Ser Ala Glu Asp Thr Phe Gln Glu Gln Asp
                325                 330                 335
Asp Ile Ser Asp Asp Val Glu Glu Val Lys Asp Gln Phe Ala Thr His
                340                 345                 350
Glu Ala Phe Met Met Glu Leu Thr Ala His Gln Ser Ser Val Gly Ser
            355                 360                 365
Val Leu Gln Ala Gly Asn Gln Leu Ile Thr Gln Gly Thr Leu Ser Asp
    370                 375                 380
Glu Glu Glu Phe Glu Ile Gln Glu Gln Met Thr Leu Leu Asn Ala Arg
385                 390                 395                 400
Trp Glu Ala Leu Arg Val Glu Ser Met Asp Arg Gln Ser Arg Leu His
                405                 410                 415
Asp Val Leu Met Glu Leu Gln Lys Lys Gln Leu Gln Gln Leu Ser Ala
                420                 425                 430
Trp Leu Thr Leu Thr Glu Glu Arg Ile Gln Lys Met Glu Thr Cys Pro
            435                 440                 445
Leu Asp Asp Asp Val Lys Ser Leu Gln Lys Leu Leu Glu Glu His Lys
    450                 455                 460
Ser Leu Gln Ser Asp Leu Glu Ala Glu Gln Val Lys Val Asn Ser Leu
465                 470                 475                 480
Thr His Met Val Val Ile Val Asp Glu Asn Ser Gly Glu Ser Ala Thr
                485                 490                 495
Ala Ile Leu Glu Asp Gln Leu Gln Lys Leu Gly Glu Arg Trp Thr Ala
            500                 505                 510
Val Cys Arg Trp Thr Glu Glu Arg Trp Asn Arg Leu Gln Glu Ile Asn
            515                 520                 525
Ile Leu Trp Gln Glu Leu Leu Glu Glu Gln Cys Leu Leu Lys Ala Trp
    530                 535                 540
Leu Thr Glu Lys Glu Glu Ala Leu Asn Lys Val Gln Thr Ser Asn Phe
545                 550                 555                 560
Lys Asp Gln Lys Glu Leu Ser Val Ser Val Arg Arg Leu Ala Ile Leu
                565                 570                 575
Lys Glu Asp Met Glu Met Lys Arg Gln Thr Leu Asp Gln Leu Ser Glu
                580                 585                 590
Ile Gly Gln Asp Val Gly Gln Leu Leu Asp Asn Ser Lys Ala Ser Lys
            595                 600                 605
Lys Ile Asn Ser Asp Ser Glu Glu Leu Thr Gln Arg Trp Asp Ser Leu
    610                 615                 620
Val Gln Arg Leu Glu Asp Ser Ser Asn Gln Val Thr Gln Ala Val Ala
625                 630                 635                 640
Lys Leu Gly Met Ser Gln Ile Pro Gln Lys Asp Leu Leu Glu Thr Val
                645                 650                 655
Arg Val Arg Glu Gln Ala Ile Thr Lys Lys Ser Lys Gln Glu Leu Pro
                660                 665                 670
Pro Pro Pro Pro Pro Lys Lys Arg Gln Ile His Val Asp Leu Glu Lys
            675                 680                 685
```

```
-continued

Leu Arg Asp Leu Gln Gly Ala Met Asp Asp Leu Asp Ala Asp Met Lys
    690                 695                 700

Glu Ala Glu Ser Val Arg Asn Gly Trp Lys Pro Val Gly Asp Leu Leu
705                 710                 715                 720

Ile Asp Ser Leu Gln Asp His Ile Glu Lys Ile Met Ala Phe Arg Glu
                725                 730                 735

Glu Ile Ala Pro Ile Asn Phe Lys Val Lys Thr Val Asn Asp Leu Ser
            740                 745                 750

Ser Gln Leu Ser Pro Leu Asp Leu His Pro Ser Leu Lys Met Ser Arg
        755                 760                 765

Gln Leu Asp Asp Leu Asn Met Arg Trp Lys Leu Leu Gln Val Ser Val
770                 775                 780

Asp Asp Arg Leu Lys Gln Leu Gln Glu Ala His Arg Asp Phe Gly Pro
785                 790                 795                 800

Ser Ser Gln His Phe Leu Ser Thr Ser Val Gln Leu Pro Trp Gln Arg
                805                 810                 815

Ser Ile Ser His Asn Lys Val Pro Tyr Tyr Ile Asn His Gln Thr Gln
            820                 825                 830

Thr Thr Cys Trp Asp His Pro Lys Met Thr Glu Leu Phe Gln Ser Leu
        835                 840                 845

Ala Asp Leu Asn Asn Val Arg Phe Ser Ala Tyr Arg Thr Ala Ile Lys
850                 855                 860

Ile Arg Arg Leu Gln Lys Ala Leu Cys Leu Asp Leu Leu Glu Leu Ser
865                 870                 875                 880

Thr Thr Asn Glu Ile Phe Lys Gln His Lys Leu Asn Gln Asn Asp Gln
                885                 890                 895

Leu Leu Ser Val Pro Asp Val Ile Asn Cys Leu Thr Thr Thr Tyr Asp
            900                 905                 910

Gly Leu Glu Gln Met His Lys Asp Leu Val Asn Val Pro Leu Cys Val
        915                 920                 925

Asp Met Cys Leu Asn Trp Leu Leu Asn Val Tyr Asp Thr Gly Arg Thr
930                 935                 940

Gly Lys Ile Arg Val Gln Ser Leu Lys Ile Gly Leu Met Ser Leu Ser
945                 950                 955                 960

Lys Gly Leu Leu Glu Glu Lys Tyr Arg Tyr Leu Phe Lys Glu Val Ala
                965                 970                 975

Gly Pro Thr Glu Met Cys Asp Gln Arg Gln Leu Gly Leu Leu Leu His
            980                 985                 990

Asp Ala Ile Gln Ile Pro Arg Gln Leu Gly Glu Val Ala Ala Phe Gly
        995                 1000                1005

Gly Ser Asn Ile Glu Pro Ser Val Arg Ser Cys Phe Gln Gln Asn
    1010                1015                1020

Asn Asn Lys Pro Glu Ile Ser Val Lys Glu Phe Ile Asp Trp Met
    1025                1030                1035

His Leu Glu Pro Gln Ser Met Val Trp Leu Pro Val Leu His Arg
    1040                1045                1050

Val Ala Ala Ala Glu Thr Ala Lys His Gln Ala Lys Cys Asn Ile
    1055                1060                1065

Cys Lys Glu Cys Pro Ile Val Gly Phe Arg Tyr Arg Ser Leu Lys
    1070                1075                1080

His Phe Asn Tyr Asp Val Cys Gln Ser Cys Phe Phe Ser Gly Arg
    1085                1090                1095

Thr Ala Lys Gly His Lys Leu His Tyr Pro Met Val Glu Tyr Cys
```

-continued

```
              1100                1105                1110
Ile Pro Thr Thr Ser Gly Glu  Asp Val Arg Asp Phe  Thr Lys Val
    1115                1120                1125

Leu Lys Asn Lys Phe Arg Ser  Lys Lys Tyr Phe Ala  Lys His Pro
    1130                1135                1140

Arg Leu Gly Tyr Leu Pro Val  Gln Thr Val Leu Glu  Gly Asp Asn
    1145                1150                1155

Leu Glu  Thr Asn
    1160

<210> SEQ ID NO 5
<211> LENGTH: 1162
<212> TYPE: PRT
<213> ORGANISM: Artificial
<220> FEATURE:
<223> OTHER INFORMATION: mouse microutrophin

<400> SEQUENCE: 5

Met Ala Lys Tyr Gly Asp Leu Glu Ala Arg Pro Asp Gly Gln Asn
1               5                   10                  15

Glu Phe Ser Asp Ile Ile Lys Ser Arg Ser Asp Glu His Asn Asp Val
                20                  25                  30

Gln Lys Lys Thr Phe Thr Lys Trp Ile Asn Ala Arg Phe Ser Lys Ser
            35                  40                  45

Gly Lys Pro Pro Ile Ser Asp Met Phe Ser Asp Leu Lys Asp Gly Arg
        50                  55                  60

Lys Leu Leu Asp Leu Leu Glu Gly Leu Thr Gly Thr Ser Leu Pro Lys
65                  70                  75                  80

Glu Arg Gly Ser Thr Arg Val His Ala Leu Asn Asn Val Asn Arg Val
                85                  90                  95

Leu Gln Val Leu His Gln Asn Asn Val Asp Leu Val Asn Ile Gly Gly
            100                 105                 110

Thr Asp Ile Val Ala Gly Asn Pro Lys Leu Thr Leu Gly Leu Leu Trp
        115                 120                 125

Ser Ile Ile Leu His Trp Gln Val Lys Asp Val Met Lys Asp Ile Met
    130                 135                 140

Ser Asp Leu Gln Gln Thr Asn Ser Glu Lys Ile Leu Leu Ser Trp Val
145                 150                 155                 160

Arg Gln Thr Thr Arg Pro Tyr Ser Gln Val Asn Val Leu Asn Phe Thr
                165                 170                 175

Thr Ser Trp Thr Asp Gly Leu Ala Phe Asn Ala Val Leu His Arg His
            180                 185                 190

Lys Pro Asp Leu Phe Asp Trp Asp Glu Met Val Lys Met Ser Pro Ile
        195                 200                 205

Glu Arg Leu Asp His Ala Phe Asp Lys Ala His Thr Ser Leu Gly Ile
    210                 215                 220

Glu Lys Leu Leu Ser Pro Glu Thr Val Ala Val His Leu Pro Asp Lys
225                 230                 235                 240

Lys Ser Ile Ile Met Tyr Leu Thr Ser Leu Phe Glu Val Leu Pro Gln
                245                 250                 255

Gln Val Thr Ile Asp Ala Ile Arg Glu Val Glu Thr Leu Pro Arg Lys
            260                 265                 270

Tyr Lys Lys Glu Cys Glu Glu Glu Ile His Ile Gln Ser Ala Val
        275                 280                 285

Leu Ala Glu Glu Gly Gln Ser Pro Arg Ala Glu Thr Pro Ser Thr Val
```

```
            290                 295                 300
Thr Glu Val Asp Met Asp Leu Asp Ser Tyr Gln Ile Ala Leu Glu Glu
305                 310                 315                 320

Val Leu Thr Trp Leu Leu Ser Ala Glu Asp Thr Phe Gln Glu Gln His
                325                 330                 335

Asp Ile Ser Asp Asp Val Glu Val Lys Glu Gln Phe Ala Thr His
                340                 345                 350

Glu Thr Phe Met Met Glu Leu Thr Ala His Gln Ser Ser Val Gly Ser
                355                 360                 365

Val Leu Gln Ala Gly Asn Gln Leu Met Thr Gln Gly Thr Leu Ser Arg
370                 375                 380

Glu Glu Glu Phe Glu Ile Gln Glu Gln Met Thr Leu Leu Asn Ala Arg
385                 390                 395                 400

Trp Glu Ala Leu Arg Val Glu Ser Met Glu Arg Gln Ser Arg Leu His
                405                 410                 415

Asp Ala Leu Met Glu Leu Gln Lys Lys Gln Leu Gln Gln Leu Ser Ser
                420                 425                 430

Trp Leu Ala Leu Thr Glu Glu Arg Ile Gln Lys Met Glu Ser Leu Pro
                435                 440                 445

Leu Gly Asp Asp Leu Pro Ser Leu Gln Lys Leu Leu Gln Glu His Lys
                450                 455                 460

Ser Leu Gln Asn Asp Leu Glu Ala Glu Gln Val Lys Val Asn Ser Leu
465                 470                 475                 480

Thr His Met Val Val Ile Val Asp Glu Asn Ser Gly Glu Ser Ala Thr
                485                 490                 495

Ala Leu Leu Glu Asp Gln Leu Gln Lys Leu Gly Glu Arg Trp Thr Ala
                500                 505                 510

Val Cys Arg Trp Thr Glu Glu Arg Trp Asn Arg Leu Gln Glu Ile Ser
                515                 520                 525

Ile Leu Trp Gln Glu Leu Leu Glu Glu Gln Cys Leu Leu Glu Ala Trp
                530                 535                 540

Leu Thr Glu Lys Glu Glu Ala Leu Asp Lys Val Gln Thr Ser Asn Phe
545                 550                 555                 560

Lys Asp Gln Lys Glu Leu Ser Val Ser Val Arg Arg Leu Ala Ile Leu
                565                 570                 575

Lys Glu Asp Met Glu Met Lys Arg Gln Thr Leu Asp Gln Leu Ser Glu
                580                 585                 590

Ile Gly Gln Asp Val Gly Gln Leu Leu Ser Asn Pro Lys Ala Ser Lys
                595                 600                 605

Lys Met Asn Ser Asp Ser Glu Glu Leu Thr Gln Arg Trp Asp Ser Leu
                610                 615                 620

Val Gln Arg Leu Glu Asp Ser Ser Asn Gln Val Thr Gln Ala Val Ala
625                 630                 635                 640

Lys Leu Gly Met Ser Gln Ile Pro Gln Lys Asp Leu Leu Glu Thr Val
                645                 650                 655

His Val Arg Glu Gln Gly Met Val Lys Lys Pro Lys Gln Glu Leu Pro
                660                 665                 670

Pro Pro Pro Pro Lys Lys Arg Gln Ile His Val Asp Leu Glu Lys
                675                 680                 685

Leu Arg Asp Leu Gln Gly Ala Met Asp Asp Leu Asp Ala Asp Met Lys
                690                 695                 700

Glu Val Glu Ala Val Arg Asn Gly Trp Lys Pro Val Gly Asp Leu Leu
705                 710                 715                 720
```

-continued

```
Ile Asp Ser Leu Gln Asp His Ile Glu Lys Thr Leu Ala Phe Arg Glu
                725                 730                 735

Glu Ile Ala Pro Ile Asn Leu Lys Val Lys Thr Met Asn Asp Leu Ser
            740                 745                 750

Ser Gln Leu Ser Pro Leu Asp Leu His Pro Ser Leu Lys Met Ser Arg
        755                 760                 765

Gln Leu Asp Asp Leu Asn Met Arg Trp Lys Leu Leu Gln Val Ser Val
    770                 775                 780

Asp Asp Arg Leu Lys Gln Leu Gln Glu Ala His Arg Asp Phe Gly Pro
785                 790                 795                 800

Ser Ser Gln His Phe Leu Ser Thr Ser Val Gln Leu Pro Trp Gln Arg
                805                 810                 815

Ser Ile Ser His Asn Lys Val Pro Tyr Tyr Ile Asn His Gln Thr Gln
            820                 825                 830

Thr Thr Cys Trp Asp His Pro Lys Met Thr Glu Leu Phe Gln Ser Leu
        835                 840                 845

Ala Asp Leu Asn Asn Val Arg Phe Ser Ala Tyr Arg Thr Ala Ile Lys
    850                 855                 860

Ile Arg Arg Leu Gln Lys Ala Leu Cys Leu Asp Leu Leu Glu Leu Asn
865                 870                 875                 880

Thr Thr Asn Glu Val Phe Lys Gln His Lys Leu Asn Gln Asn Asp Gln
                885                 890                 895

Leu Leu Ser Val Pro Asp Val Ile Asn Cys Leu Thr Thr Thr Tyr Asp
            900                 905                 910

Gly Leu Glu Gln Leu His Lys Asp Leu Val Asn Val Pro Leu Cys Val
        915                 920                 925

Asp Met Cys Leu Asn Trp Leu Leu Asn Val Tyr Asp Thr Gly Arg Thr
    930                 935                 940

Gly Lys Ile Arg Val Gln Ser Leu Lys Ile Gly Leu Met Ser Leu Ser
945                 950                 955                 960

Lys Gly Leu Leu Glu Glu Lys Tyr Arg Cys Leu Phe Lys Glu Val Ala
                965                 970                 975

Gly Pro Thr Glu Met Cys Asp Gln Arg Gln Leu Gly Leu Leu Leu His
            980                 985                 990

Asp Ala Ile Gln Ile Pro Arg Gln Leu Gly Glu Val Ala Ala Phe Gly
        995                 1000                1005

Gly Ser Asn Ile Glu Pro Ser Val Arg Ser Cys Phe Gln Gln Asn
    1010                1015                1020

Asn Asn Lys Pro Glu Ile Ser Val Lys Glu Phe Ile Asp Trp Met
    1025                1030                1035

His Leu Glu Pro Gln Ser Met Val Trp Leu Pro Val Leu His Arg
    1040                1045                1050

Val Ala Ala Glu Thr Ala Lys His Gln Ala Lys Cys Asn Ile
    1055                1060                1065

Cys Lys Glu Cys Pro Ile Val Gly Phe Arg Tyr Arg Ser Leu Lys
    1070                1075                1080

His Phe Asn Tyr Asp Val Cys Gln Ser Cys Phe Phe Ser Gly Arg
    1085                1090                1095

Thr Ala Lys Gly His Lys Leu His Tyr Pro Met Val Glu Tyr Cys
    1100                1105                1110

Ile Pro Thr Thr Ser Gly Glu Asp Val Arg Asp Phe Thr Lys Val
    1115                1120                1125
```

-continued

| Leu | Lys | Asn | Lys | Phe | Arg | Ser | Lys | Lys | Tyr | Phe | Ala | Lys | His | Pro |
|---|---|---|---|---|---|---|---|---|---|---|---|---|---|---|
| 1130 | | | | 1135 | | | | | 1140 | | | | | |

| Arg | Leu | Gly | Tyr | Leu | Pro | Val | Gln | Thr | Val | Leu | Glu | Gly | Asp | Asn |
|---|---|---|---|---|---|---|---|---|---|---|---|---|---|---|
| 1145 | | | | | 1150 | | | | | 1155 | | | | |

| Leu | Glu | Thr | Asn |
|---|---|---|---|
| 1160 | | | |

<210> SEQ ID NO 6
<211> LENGTH: 3486
<212> TYPE: DNA
<213> ORGANISM: artificial
<220> FEATURE:
<223> OTHER INFORMATION: human  microutrophin
<400> SEQUENCE: 6

```
atggccaagt atggagaaca tgaagccagt cctgacaatg gcagaacga attcagtgat      60
atcattaagt ccagatctga tgaacacaat gacgtacaga agaaaacctt taccaaatgg    120
ataaatgctc gattttcaaa gagtgggaaa ccacccatca atgatatgtt cacagacctc    180
aaagatggaa ggaagctatt ggatcttcta gaaggcctca caggaacatc actgccaaag    240
gaacgtggtt ccacaagggt acatgcctta ataacgtca acagagtgct gcaggtttta    300
catcagaaca atgtgaatt agtgaatata ggggaactg acattgtgga tggaaatcac    360
aaactgactt tggggttact ttggagcatc attttgcact ggcaggtgaa agatgtcatg    420
aaggatgtca tgtcggacct gcagcagacg aacagtgaga agatcctgct cagctgggtg    480
cgtcagacca ccaggcccta cagccaagtc aacgtcctca acttcaccac cagctggaca    540
gatggactcg cctttaatgc tgtcctccac cgacataaac ctgatctctt cagctgggat    600
aaagttgtca aatgtcacc aattgagaga cttgaacatg ccttcagcaa ggctcaaact    660
tatttgggaa ttgaaaagct gttagatcct gaagatgttg ccgttcggct tcctgacaag    720
aaatccataa ttatgtattt aacatctttg tttgaggtgc acctcagca agtcaccata    780
gacgccatcc gtgaggtaga gacactccca aggaaatata aaaagaatg tgaagaagag    840
gcaattaata tacagagtac agcgcctgag gaggagcatg agagtccccg agctgaaact    900
cccagcactg tcactgaggt cgacatggat ctggacagct atcagattgc gttggaggaa    960
gtgctgacct ggtgctttc tgctgaggac acttccagg agcaggatga tatttctgat   1020
gatgttgaag aagtcaaaga ccagtttgca acccatgaag cttttatgat ggaactgact   1080
gcacaccaga gcagtgtggg cagcgtcctg caggcaggca accaactgat aacacaagga   1140
actctgtcag acgaagaaga atttgagatt caggaacaga tgacccctgct gaatgctaga   1200
tgggaggctc ttagggtgga gagtatggac agacagtccc ggctgcacga tgtgctgatg   1260
gaactgcaga gaagcaact gcagcagctc tccgcctggt taacactcac agaggagcgc   1320
attcagaaga tggaaacttg ccccctggat gatgatgtaa atctctacac aaagctgcta   1380
gaagaacata aaagttcgca agtgatctt gaggctgaac aggtgaaagt aaattcacta   1440
actcacatgg tggtcattgt tgatgaaaac agtggtgaga cgctacagc tatcctagaa   1500
gaccagttac agaaacttgg tgagcgctgg acagcagtat gccgttggac tgaagaacgc   1560
tggaataggt acaagaaat caatatattg gcaggaat tattggaaga cagtgcttg   1620
ttgaaagctt ggttaaccga aaagagaag ctttaaata agtccagac aagcaacttc   1680
aaagaccaaa aggaactaag tgtcagtgtt cgacgtctgg ctattttgaa ggaagacatg   1740
gaaatgaagc gtcaaacatt ggatcagctg agtgagattg ccaggatgt gggacaatta   1800
```

-continued

```
cttgataatt ccaaggcatc taagaagatc aacagtgact cagaggaact gactcaaaga    1860
tgggattctt tggttcagag actagaagat tcctccaacc aggtgactca ggctgtagca    1920
aagctgggga tgtctcagat tcctcagaag gaccttttgg agactgttcg tgtaagagaa    1980
caagcaatta caaaaaaatc taagcaggaa ctgcctcctc ctcctccccc aaagaagaga    2040
cagatccatg tggatttgga gaaactcaga gacctgcagg gagctatgga tgacctggac    2100
gctgacatga aggaggcaga gtccgtgcgg aatggctgga gcccgtggg agacttactc     2160 attgactcgc tgcaggatca cattgaaaaa atcatggcat ttagagaaga aattgcacca    2220
atcaacttta aagttaaaac ggtgaatgat ttatccagtc agctgtctcc acttgacctg    2280
catccctctc taaagatgtc tcgccagcta gatgacctta atatgcgatg gaaacttta    2340 caggtttctg tggatgatcg ccttaaacag cttcaggaag cccacagaga ttttggacca    2400
tcctctcagc attttctctc tacgtcagtc cagctgccgt ggcaaagatc catttcacat    2460
aataaagtgc cctattacat caaccatcaa acacagacca cctgttggga ccatcctaaa    2520
atgaccgaac tctttcaatc ccttgctgac ctgaataatg tacgtttttc tgcctaccgt    2580
acagcaatca aaatccgaag actacaaaaa gcactatgtt tggatctctt agagttgagt    2640
acaacaaatg aaattttcaa acagcacaag ttgaaccaaa atgaccagct cctcagtgtt    2700
ccagatgtca tcaactgtct gacaacaact tatgatggac ttgagcaaat gcataaggac    2760
ctggtcaacg ttccactctg tgttgatatg tgtctcaatt ggttgctcaa tgtctatgac    2820
acgggtcgaa ctggaaaaat tagagtgcag agtctgaaga ttggattaat gtctctctcc    2880
aaaggtctct tggaagaaaa atacagatat ctctttaagg aagttgcggg gccgacagaa    2940
atgtgtgacc agaggcagct gggcctgtta cttcatgatg ccatccagat cccccggcag    3000
ctaggtgaag tagcagcttt tggaggcagt aatattgagc ctagtgttcg cagctgcttc    3060
caacagaata caataaaacc agaaataagt gtgaaagagt ttatagattg gatgcatttg    3120
gaaccacagt ccatggtttg gctcccagtt ttacatcgag tggcagcagc ggagactgca    3180
aaacatcagg ccaaatgcaa catctgtaaa gaatgtccaa ttgtcgggtt caggtataga    3240
agccttaagc attttaacta tgatgtctgc cagagttgtt tcttttcggg tcgaacagca    3300
aaaggtcaca aattacatta cccaatggtg gaatattgta tacctacaac atctggggaa    3360
gatgtacgag acttcacaaa ggtacttaag aacaagttca ggtcgaagaa gtactttgcc    3420 aaacacccctc gacttggtta cctgcctgtc cagacagttc ttgaaggtga caacttagag    3480
acttga                                                              3486
```

<210> SEQ ID NO 7
<211> LENGTH: 3486
<212> TYPE: DNA
<213> ORGANISM: artificial
<220> FEATURE:
<223> OTHER INFORMATION: mouse microutrophin

<400> SEQUENCE: 7

```
atggccaagt atgggggacct tgaagccagg cctgatgatg ggcagaacga attcagtgac      60
atcattaagt ccagatctga tgaacacaat gatgtacaga agaaaacctt taccaaatgg       120
ataaacgctc gattttccaa gagtgggaaa ccacccatca gtgatatgtt ctcagacctc      180
aaagatggga gaaagctctc tggatcttct gaaggcctca caggaacatc attgccaaag      240
gaacgtggtt ccacaagggt gcatgcctta acaatgtca accgagtgct acaggtttta      300
catcagaaca atgtggactt ggtgaatatt ggaggcacgg acattgtggc tggaaatccc      360
```

-continued

```
aagctgactt tagggttact ctggagcatc attctgcact ggcaggtgaa ggatgtcatg    420
aaagatatca tgtcagacct gcagcagaca acagcgaga  agatcctgct gagctgggtg    480
cggcagacca ccaggcccta cagtcaagtc aacgtcctca acttcaccac cagctggacc    540
gatggactcg cgttcaacgc cgtgctccac cggcacaaac cagatctctt cgactgggac    600
gagatggtca aaatgtcccc aattgagaga cttgaccatg cttttgacaa ggcccacact    660
tctttgggaa ttgaaaagct cctaagtcct gaaactgttg ctgtgcatct ccctgacaag    720
aaatccataa ttatgtattt aacgtctctg tttgaggtgc ttcctcagca agtcacgata    780
gatgccatcc gagaggtgga gactctccca aggaagtata agaaagaatg tgaagaggaa    840
gaaattcata tccagagtgc agtgctggca gaggaaggcc agagtccccg agctgagacc    900
cctagcaccg tcactgaagt ggacatggat ttggacagct accagatagc gctagaggaa    960
gtgctgacgt ggctgctgtc cgcggaggac acgttccagg agcaacatga catttctgat   1020
gatgtcgaag aagtcaaaga gcagtttgct acccatgaaa cttttatgat ggagctgaca   1080
gcacaccaga gcagcgtggg gagcgtcctg caggctggca accagctgat gacacaaggg   1140
actctgtcca gagaggagga gtttgagatc caggaacaga tgaccttgct gaatgcaagg   1200
tgggaggcgc tccgggtgga gagcatggag aggcagtccc ggctgcacga cgctctgatg   1260
gagctgcaga agaaacagct gcagcagctc tcaagctggc tggccctcac agaagagcgc   1320
attcagaaga tggagagcct cccgctgggt gatgacctgc cctccctgca gaagctgctt   1380
caagaacata aaagtttgca aaatgacctt gaagctgaac aggtgaaggt aaattcctta   1440
actcacatgg tggtgattgt ggatgaaaac agtggggaga gtgccacagc tcttctggaa   1500
gatcagttac agaaactggg tgagcgctgg acagctgtat gccgctggac tgaagaacgt   1560
tggaacaggt tgcaagaaat cagtattctg tggcaggaat tattggaaga gcagtgtctg   1620
ttggaggctt ggctcaccga aaaggaagag gcttttggata agttcaaaac cagcaacttt   1680
aaagaccaga aggaactaag tgtcagtgtc cggcgtctgg ctatattgaa ggaagacatg   1740
gaaatgaaga ggcagactct ggatcaactg agtgagattg ccaggatgt  gggccaatta   1800 ctcagtaatc ccaaggcatc taagaagatg aacagtgact ctgaggagct aacacagaga   1860
tgggattctc tggttcagag actcgaagac tcttctaacc aggtgactca ggcggtagcg   1920
aagctcggca tgtcccagat tccacagaag gacctattgg agaccgttca tgtgagagaa   1980
caagggatgg tgaagaagcc caagcaggaa ctgcctcctc ctcccccacc aaagaagaga   2040
cagattcacg tggacttaga gaaactccga gacctgcagg gagctatgga cgacctggac   2100
gcagacatga aggaggtgga ggctgtgcgg aatggctgga agcccgtggg agacctgctt   2160
atagactccc tgcaggatca catcgagaaa accctggcgt ttagagaaga aattgcacca   2220
atcaacttaa aagtaaaaac aatgaatgac ctgtccagtc agctgtctcc acttgacttg   2280
catccatctc taaagatgtc tcgccagctg gatgacctta atatgcgatg gaaacttcta   2340
caggtttccg tggacgatcg ccttaagcag ctccaggaag cccacagaga ttttgggcca   2400
tcttctcaac actttctgtc cacttcagtc cagctgccgt ggcagagatc catttcacat   2460
aataaagtgc cctattacat caaccatcaa acacagacaa cctgttggga tcatcctaaa   2520
atgactgagc tcttccaatc ccttgctgat ctgaataatg tacgtttctc tgcctaccgc   2580
acagcaatca aaattcgaag gctgcaaaaa gcattatgtc tggatctctt agagctgaat   2640
acgacgaatg aagttttcaa gcagcacaaa ctgaaccaaa atgatcagct cctgagtgtc   2700
```

-continued

```
ccagacgtca tcaactgtct gaccaccact tacgatgggc ttgagcagct gcacaaggac    2760
ttggtcaatg ttccactctg cgtcgatatg tgtctcaact ggctgctcaa cgtatacgac    2820
acgggccgga ctggaaaaat tcgggtacag agtctgaaga ttggattgat gtctctctcc    2880
aaaggcctct tagaagagaa atacagatgt ctctttaagg aggtggcagg gccaactgag    2940
atgtgtgacc agcggcagct tggcctgcta cttcacgatg ccatccagat ccctaggcag    3000
ctgggggaag tagcagcctt tggggcagt aacattgagc ccagtgtccg cagctgcttc    3060
cagcagaata caacaagcc agaaatcagt gtgaaggagt ttatagactg gatgcatttg    3120 gaacccagt ccatggtgtg gttgccggtt ctgcatcggg tcgcagctgc tgagactgca    3180
aaacatcagg ccaaatgcaa catctgcaaa gaatgcccga ttgttgggtt cagatacagg    3240
agcctaaagc attttaatta tgatgtctgc cagagttgct tctttctgg aagaacagca    3300 aagggccaca agttacatta cccgatggta gaatactgca taccgacaac atctggggaa    3360
gatgtgagag atttcactaa ggtgctgaag aacaagttca ggtccaagaa atattttgcc    3420
aaacatcctc ggcttggcta cctgcctgtc cagaccgtgc tggaagggga caacttagaa    3480
acttga                                                              3486
```

<210> SEQ ID NO 8
<211> LENGTH: 3684
<212> TYPE: PRT
<213> ORGANISM: Human Dystrophin

<400> SEQUENCE: 8

```
Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Val Asn Lys Ala
65                  70                  75                  80

Leu Arg Val Leu Asn Asn Asn Val Asp Leu Val Asn Ile Gly Ser Thr
                85                  90                  95

Asp Ile Val Asp Gly Asn His Lys Leu Thr Leu Gly Leu Ile Trp Asn
            100                 105                 110

Ile Ile Leu His Trp Gln Val Lys Asn Val Met Lys Asn Ile Met Ala
        115                 120                 125

Gly Leu Gln Gln Thr Asn Ser Glu Lys Ile Leu Leu Ser Trp Val Arg
    130                 135                 140

Gln Ser Thr Arg Asn Tyr Pro Gln Val Asn Val Ile Asn Phe Thr Thr
145                 150                 155                 160

Ser Trp Ser Asp Gly Leu Ala Leu Asn Ala Leu Ile His Ser His Arg
                165                 170                 175

Pro Asp Leu Phe Asp Trp Asn Ser Val Val Cys Gln Gln Ser Ala Thr
            180                 185                 190

Gln Arg Leu Glu His Ala Phe Asn Ile Ala Arg Tyr Gln Leu Gly Ile
        195                 200                 205

Glu Lys Leu Leu Asp Pro Glu Asp Val Asp Thr Thr Tyr Pro Asp Lys
    210                 215                 220

Lys Ser Ile Leu Met Tyr Ile Thr Ser Leu Phe Gln Val Leu Pro Gln
```

```
            225                 230                 235                 240
Gln Val Ser Ile Glu Ala Ile Gln Glu Val Glu Met Leu Pro Arg Pro
                245                 250                 255
Pro Lys Val Thr Lys Glu Glu His Phe Gln Leu His His Gln Met His
            260                 265                 270
Tyr Ser Gln Gln Ile Thr Val Ser Leu Ala Gln Gly Tyr Glu Arg Thr
            275                 280                 285
Ser Ser Pro Lys Pro Arg Phe Lys Ser Tyr Ala Tyr Thr Gln Ala Ala
        290                 295                 300
Tyr Val Thr Thr Ser Asp Pro Thr Arg Ser Pro Phe Pro Ser Gln His
305                 310                 315                 320
Leu Glu Ala Pro Glu Asp Lys Ser Phe Gly Ser Ser Leu Met Glu Ser
                325                 330                 335
Glu Val Asn Leu Asp Arg Tyr Gln Thr Ala Leu Glu Glu Val Leu Ser
            340                 345                 350
Trp Leu Leu Ser Ala Glu Asp Thr Leu Gln Ala Gln Gly Glu Ile Ser
            355                 360                 365
Asn Asp Val Glu Val Lys Asp Gln Phe His Thr His Glu Gly Tyr
        370                 375                 380
Met Met Asp Leu Thr Ala His Gln Gly Arg Val Gly Asn Ile Leu Gln
385                 390                 395                 400
Leu Gly Ser Lys Leu Ile Gly Thr Gly Lys Leu Ser Glu Asp Glu Glu
                405                 410                 415
Thr Glu Val Gln Glu Gln Met Asn Leu Leu Asn Ser Arg Trp Glu Cys
            420                 425                 430
Leu Arg Val Ala Ser Met Glu Lys Gln Ser Asn Leu His Arg Val Leu
            435                 440                 445
Met Asp Leu Gln Asn Gln Lys Leu Lys Glu Leu Asn Asp Trp Leu Thr
        450                 455                 460
Lys Thr Glu Glu Arg Thr Arg Lys Met Glu Glu Pro Leu Gly Pro
465                 470                 475                 480
Asp Leu Glu Asp Leu Lys Arg Gln Val Gln Gln His Lys Val Leu Gln
                485                 490                 495
Glu Asp Leu Glu Gln Glu Gln Val Arg Val Asn Ser Leu Thr His Met
            500                 505                 510
Val Val Val Val Asp Glu Ser Ser Gly Asp His Ala Thr Ala Ala Leu
            515                 520                 525
Glu Glu Gln Leu Lys Val Leu Gly Asp Arg Trp Ala Asn Ile Cys Arg
        530                 535                 540
Trp Thr Glu Asp Arg Trp Val Leu Leu Gln Asp Ile Leu Leu Lys Trp
545                 550                 555                 560
Gln Arg Leu Thr Glu Glu Gln Cys Leu Phe Ser Ser Trp Leu Ser Glu
                565                 570                 575
Lys Glu Asp Ala Val Asn Lys Ile His Thr Thr Gly Phe Lys Asp Gln
            580                 585                 590
Asn Glu Met Leu Ser Ser Leu Gln Lys Leu Ala Val Leu Lys Ala Asp
            595                 600                 605
Leu Glu Lys Lys Lys Gln Ser Met Gly Lys Leu Tyr Ser Leu Lys Gln
        610                 615                 620
Asp Leu Leu Ser Thr Leu Lys Asn Lys Ser Val Thr Gln Lys Thr Glu
625                 630                 635                 640
Ala Trp Leu Asp Asn Phe Ala Arg Cys Trp Asp Asn Leu Val Gln Lys
                645                 650                 655
```

```
Leu Glu Lys Ser Thr Ala Gln Ile Ser Gln Ala Val Thr Thr Thr Gln
                660                 665                 670

Pro Ser Leu Thr Gln Thr Thr Val Met Glu Thr Val Thr Thr Val Thr
            675                 680                 685

Thr Arg Glu Gln Ile Leu Val Lys His Ala Gln Glu Glu Leu Pro Pro
        690                 695                 700

Pro Pro Pro Gln Lys Lys Arg Gln Ile Thr Val Asp Ser Glu Ile Arg
705                 710                 715                 720

Lys Arg Leu Asp Val Asp Ile Thr Glu Leu His Ser Trp Ile Thr Arg
                725                 730                 735

Ser Glu Ala Val Leu Gln Ser Pro Glu Phe Ala Ile Phe Arg Lys Glu
            740                 745                 750

Gly Asn Phe Ser Asp Leu Lys Glu Lys Val Asn Ala Ile Glu Arg Glu
        755                 760                 765

Lys Ala Glu Lys Phe Arg Lys Leu Gln Asp Ala Ser Arg Ser Ala Gln
770                 775                 780

Ala Leu Val Glu Gln Met Val Asn Glu Gly Val Asn Ala Asp Ser Ile
785                 790                 795                 800

Lys Gln Ala Ser Glu Gln Leu Asn Ser Arg Trp Ile Glu Phe Cys Gln
                805                 810                 815

Leu Leu Ser Glu Arg Leu Asn Trp Leu Glu Tyr Gln Asn Asn Ile Ile
            820                 825                 830

Ala Phe Tyr Asn Gln Leu Gln Gln Leu Glu Gln Met Thr Thr Thr Ala
        835                 840                 845

Glu Asn Trp Leu Lys Ile Gln Pro Thr Thr Pro Ser Glu Pro Thr Ala
850                 855                 860

Ile Lys Ser Gln Leu Lys Ile Cys Lys Asp Glu Val Asn Arg Leu Ser
865                 870                 875                 880

Gly Leu Gln Pro Gln Ile Glu Arg Leu Lys Ile Gln Ser Ile Ala Leu
                885                 890                 895

Lys Glu Lys Gly Gln Gly Pro Met Phe Leu Asp Ala Asp Phe Val Ala
            900                 905                 910

Phe Thr Asn His Phe Lys Gln Val Phe Ser Asp Val Gln Ala Arg Glu
        915                 920                 925

Lys Glu Leu Gln Thr Ile Phe Asp Thr Leu Pro Pro Met Arg Tyr Gln
    930                 935                 940

Glu Thr Met Ser Ala Ile Arg Thr Trp Val Gln Gln Ser Glu Thr Lys
945                 950                 955                 960

Leu Ser Ile Pro Gln Leu Ser Val Thr Asp Tyr Glu Ile Met Glu Gln
                965                 970                 975

Arg Leu Gly Glu Leu Gln Ala Leu Gln Ser Ser Leu Gln Glu Gln Gln
            980                 985                 990

Ser Gly Leu Tyr Tyr Leu Ser Thr Thr Val Lys Glu Met Ser Lys Lys
        995                1000                1005

Ala Pro Ser Glu Ile Ser Arg Lys Tyr Gln Ser Glu Phe Glu Glu
    1010                1015                1020

Ile Glu Gly Arg Trp Lys Lys Leu Ser Ser Gln Leu Val Glu His
    1025                1030                1035

Cys Gln Lys Leu Glu Glu Gln Met Asn Lys Leu Arg Lys Ile Gln
    1040                1045                1050

Asn His Ile Gln Thr Leu Lys Lys Trp Met Ala Glu Val Asp Val
    1055                1060                1065
```

-continued

```
Phe Leu Lys Glu Glu Trp Pro Ala Leu Gly Asp Ser Glu Ile Leu
    1070                1075                1080

Lys Lys Gln Leu Lys Gln Cys Arg Leu Leu Val Ser Asp Ile Gln
    1085                1090                1095

Thr Ile Gln Pro Ser Leu Asn Ser Val Asn Glu Gly Gly Gln Lys
    1100                1105                1110

Ile Lys Asn Glu Ala Glu Pro Glu Phe Ala Ser Arg Leu Glu Thr
    1115                1120                1125

Glu Leu Lys Glu Leu Asn Thr Gln Trp Asp His Met Cys Gln Gln
    1130                1135                1140

Val Tyr Ala Arg Lys Glu Ala Leu Lys Gly Gly Leu Glu Lys Thr
    1145                1150                1155

Val Ser Leu Gln Lys Asp Leu Ser Glu Met His Glu Trp Met Thr
    1160                1165                1170

Gln Ala Glu Glu Glu Tyr Leu Glu Arg Asp Phe Glu Tyr Lys Thr
    1175                1180                1185

Pro Asp Glu Leu Gln Lys Ala Val Glu Glu Met Lys Arg Ala Lys
    1190                1195                1200

Glu Glu Ala Gln Gln Lys Glu Ala Lys Val Lys Leu Leu Thr Glu
    1205                1210                1215

Ser Val Asn Ser Val Ile Ala Gln Ala Pro Pro Val Ala Gln Glu
    1220                1225                1230

Ala Leu Lys Lys Glu Leu Glu Thr Leu Thr Thr Asn Tyr Gln Trp
    1235                1240                1245

Leu Cys Thr Arg Leu Asn Gly Lys Cys Lys Thr Leu Glu Glu Val
    1250                1255                1260

Trp Ala Cys Trp His Glu Leu Leu Ser Tyr Leu Glu Lys Ala Asn
    1265                1270                1275

Lys Trp Leu Asn Glu Val Glu Phe Lys Leu Lys Thr Thr Glu Asn
    1280                1285                1290

Ile Pro Gly Gly Ala Glu Glu Ile Ser Glu Val Leu Asp Ser Leu
    1295                1300                1305

Glu Asn Leu Met Arg His Ser Glu Asp Asn Pro Asn Gln Ile Arg
    1310                1315                1320

Ile Leu Ala Gln Thr Leu Thr Asp Gly Gly Val Met Asp Glu Leu
    1325                1330                1335

Ile Asn Glu Glu Leu Glu Thr Phe Asn Ser Arg Trp Arg Glu Leu
    1340                1345                1350

His Glu Glu Ala Val Arg Arg Gln Lys Leu Leu Glu Gln Ser Ile
    1355                1360                1365

Gln Ser Ala Gln Glu Thr Glu Lys Ser Leu His Leu Ile Gln Glu
    1370                1375                1380

Ser Leu Thr Phe Ile Asp Lys Gln Leu Ala Ala Tyr Ile Ala Asp
    1385                1390                1395

Lys Val Asp Ala Ala Gln Met Pro Gln Glu Ala Gln Lys Ile Gln
    1400                1405                1410

Ser Asp Leu Thr Ser His Glu Ile Ser Leu Glu Glu Met Lys Lys
    1415                1420                1425

His Asn Gln Gly Lys Glu Ala Ala Gln Arg Val Leu Ser Gln Ile
    1430                1435                1440

Asp Val Ala Gln Lys Lys Leu Gln Asp Val Ser Met Lys Phe Arg
    1445                1450                1455

Leu Phe Gln Lys Pro Ala Asn Phe Glu Leu Arg Leu Gln Glu Ser
```

-continued

```
                1460                1465                1470

Lys Met Ile Leu Asp Glu Val Lys Met His Leu Pro Ala Leu Glu
    1475                1480                1485

Thr Lys Ser Val Glu Gln Glu Val Val Gln Ser Gln Leu Asn His
    1490                1495                1500

Cys Val Asn Leu Tyr Lys Ser Leu Ser Glu Val Lys Ser Glu Val
    1505                1510                1515

Glu Met Val Ile Lys Thr Gly Arg Gln Ile Val Gln Lys Lys Gln
    1520                1525                1530

Thr Glu Asn Pro Lys Glu Leu Asp Glu Arg Val Thr Ala Leu Lys
    1535                1540                1545

Leu His Tyr Asn Glu Leu Gly Ala Lys Val Thr Glu Arg Lys Gln
    1550                1555                1560

Gln Leu Glu Lys Cys Leu Lys Leu Ser Arg Lys Met Arg Lys Glu
    1565                1570                1575

Met Asn Val Leu Thr Glu Trp Leu Ala Ala Thr Asp Met Glu Leu
    1580                1585                1590

Thr Lys Arg Ser Ala Val Glu Gly Met Pro Ser Asn Leu Asp Ser
    1595                1600                1605

Glu Val Ala Trp Gly Lys Ala Thr Gln Lys Glu Ile Glu Lys Gln
    1610                1615                1620

Lys Val His Leu Lys Ser Ile Thr Glu Val Gly Glu Ala Leu Lys
    1625                1630                1635

Thr Val Leu Gly Lys Lys Glu Thr Leu Val Glu Asp Lys Leu Ser
    1640                1645                1650

Leu Leu Asn Ser Asn Trp Ile Ala Val Thr Ser Arg Ala Glu Glu
    1655                1660                1665

Trp Leu Asn Leu Leu Leu Glu Tyr Gln Lys His Met Glu Thr Phe
    1670                1675                1680

Asp Gln Asn Val Asp His Ile Thr Lys Trp Ile Ile Gln Ala Asp
    1685                1690                1695

Thr Leu Leu Asp Glu Ser Glu Lys Lys Lys Pro Gln Gln Lys Glu
    1700                1705                1710

Asp Val Leu Lys Arg Leu Lys Ala Glu Leu Asn Asp Ile Arg Pro
    1715                1720                1725

Lys Val Asp Ser Thr Arg Asp Gln Ala Ala Asn Leu Met Ala Asn
    1730                1735                1740

Arg Gly Asp His Cys Arg Lys Leu Val Glu Pro Gln Ile Ser Glu
    1745                1750                1755

Leu Asn His Arg Phe Ala Ala Ile Ser His Arg Ile Lys Thr Gly
    1760                1765                1770

Lys Ala Ser Ile Pro Leu Lys Glu Leu Glu Gln Phe Asn Ser Asp
    1775                1780                1785

Ile Gln Lys Leu Leu Glu Pro Leu Glu Ala Glu Ile Gln Gln Gly
    1790                1795                1800

Val Asn Leu Lys Glu Glu Asp Phe Asn Lys Asp Met Asn Glu Asp
    1805                1810                1815

Asn Glu Gly Thr Val Lys Glu Leu Leu Gln Arg Gly Asp Asn Leu
    1820                1825                1830

Gln Gln Arg Ile Thr Asp Glu Arg Lys Arg Glu Glu Ile Lys Ile
    1835                1840                1845

Lys Gln Gln Leu Leu Gln Thr Lys His Asn Ala Leu Lys Asp Leu
    1850                1855                1860
```

-continued

```
Arg Ser Gln Arg Arg Lys Lys Ala Leu Glu Ile Ser His Gln Trp
    1865            1870                1875
Tyr Gln Tyr Lys Arg Gln Ala Asp Asp Leu Leu Lys Cys Leu Asp
    1880            1885                1890
Asp Ile Glu Lys Lys Leu Ala Ser Leu Pro Glu Pro Arg Asp Glu
    1895            1900                1905
Arg Lys Ile Lys Glu Ile Asp Arg Glu Leu Gln Lys Lys Lys Glu
    1910            1915                1920
Glu Leu Asn Ala Val Arg Arg Gln Ala Glu Gly Leu Ser Glu Asp
    1925            1930                1935
Gly Ala Ala Met Ala Val Glu Pro Thr Gln Ile Gln Leu Ser Asp
    1940            1945                1950
Arg Trp Arg Glu Ile Glu Ser Lys Phe Ala Gln Phe Arg Arg Leu
    1955            1960                1965
Asn Phe Ala Gln Ile His Thr Val Arg Glu Glu Thr Met Met Val
    1970            1975                1980
Met Thr Glu Asp Met Pro Leu Glu Ile Ser Tyr Val Pro Ser Thr
    1985            1990                1995
Tyr Leu Thr Glu Ile Thr His Val Ser Gln Ala Leu Leu Glu Val
    2000            2005                2010
Glu Gln Leu Leu Asn Ala Pro Asp Leu Cys Ala Lys Asp Phe Glu
    2015            2020                2025
Asp Leu Phe Lys Gln Glu Glu Ser Leu Lys Asn Ile Lys Asp Ser
    2030            2035                2040
Leu Gln Gln Ser Ser Gly Arg Ile Asp Ile Ile His Ser Lys Lys
    2045            2050                2055
Thr Ala Ala Leu Gln Ser Ala Thr Pro Val Glu Arg Val Lys Leu
    2060            2065                2070
Gln Glu Ala Leu Ser Gln Leu Asp Phe Gln Trp Glu Lys Val Asn
    2075            2080                2085
Lys Met Tyr Lys Asp Arg Gln Gly Arg Phe Asp Arg Ser Val Glu
    2090            2095                2100
Lys Trp Arg Arg Phe His Tyr Asp Ile Lys Ile Phe Asn Gln Trp
    2105            2110                2115
Leu Thr Glu Ala Glu Gln Phe Leu Arg Lys Thr Gln Ile Pro Glu
    2120            2125                2130
Asn Trp Glu His Ala Lys Tyr Lys Trp Tyr Leu Lys Glu Leu Gln
    2135            2140                2145
Asp Gly Ile Gly Gln Arg Gln Thr Val Val Arg Thr Leu Asn Ala
    2150            2155                2160
Thr Gly Glu Glu Ile Ile Gln Gln Ser Ser Lys Thr Asp Ala Ser
    2165            2170                2175
Ile Leu Gln Glu Lys Leu Gly Ser Leu Asn Leu Arg Trp Gln Glu
    2180            2185                2190
Val Cys Lys Gln Leu Ser Asp Arg Lys Lys Arg Leu Glu Glu Gln
    2195            2200                2205
Lys Asn Ile Leu Ser Glu Phe Gln Arg Asp Leu Asn Glu Phe Val
    2210            2215                2220
Leu Trp Leu Glu Glu Ala Asp Asn Ile Ala Ser Ile Pro Leu Glu
    2225            2230                2235
Pro Gly Lys Glu Gln Gln Leu Lys Glu Lys Leu Glu Gln Val Lys
    2240            2245                2250
```

```
Leu Leu Val Glu Glu Leu Pro Leu Arg Gln Gly Ile Leu Lys Gln
    2255                2260                2265

Leu Asn Glu Thr Gly Gly Pro Val Leu Val Ser Ala Pro Ile Ser
    2270                2275                2280

Pro Glu Glu Gln Asp Lys Leu Glu Asn Lys Leu Lys Gln Thr Asn
    2285                2290                2295

Leu Gln Trp Ile Lys Val Ser Arg Ala Leu Pro Glu Lys Gln Gly
    2300                2305                2310

Glu Ile Glu Ala Gln Ile Lys Asp Leu Gly Gln Leu Glu Lys Lys
    2315                2320                2325

Leu Glu Asp Leu Glu Glu Gln Leu Asn His Leu Leu Leu Trp Leu
    2330                2335                2340

Ser Pro Ile Arg Asn Gln Leu Glu Ile Tyr Asn Gln Pro Asn Gln
    2345                2350                2355

Glu Gly Pro Phe Asp Val Gln Glu Thr Glu Ile Ala Val Gln Ala
    2360                2365                2370

Lys Gln Pro Asp Val Glu Glu Ile Leu Ser Lys Gly Gln His Leu
    2375                2380                2385

Tyr Lys Glu Glu Pro Ala Thr Gln Pro Val Lys Arg Lys Leu Glu
    2390                2395                2400

Asp Leu Ser Ser Glu Trp Lys Ala Val Asn Arg Leu Leu Gln Glu
    2405                2410                2415

Leu Arg Ala Lys Gln Pro Asp Leu Ala Pro Gly Leu Thr Thr Ile
    2420                2425                2430

Gly Ala Ser Pro Thr Gln Thr Val Thr Leu Val Thr Gln Pro Val
    2435                2440                2445

Val Thr Lys Glu Thr Ala Ile Ser Lys Leu Glu Met Pro Ser Ser
    2450                2455                2460

Leu Met Leu Glu Val Pro Ala Leu Ala Asp Phe Asn Arg Ala Trp
    2465                2470                2475

Thr Glu Leu Thr Asp Trp Leu Ser Leu Leu Asp Gln Val Ile Lys
    2480                2485                2490

Ser Gln Arg Val Met Val Gly Asp Leu Glu Asp Ile Asn Glu Met
    2495                2500                2505

Ile Ile Lys Gln Lys Ala Thr Met Gln Asp Leu Glu Gln Arg Arg
    2510                2515                2520

Pro Gln Leu Glu Glu Leu Ile Thr Ala Ala Gln Asn Leu Lys Asn
    2525                2530                2535

Lys Thr Ser Asn Gln Glu Ala Arg Thr Ile Ile Thr Asp Arg Ile
    2540                2545                2550

Glu Arg Ile Gln Asn Gln Trp Asp Glu Val Gln Glu His Leu Gln
    2555                2560                2565

Asn Arg Arg Gln Gln Leu Asn Glu Met Leu Lys Asp Ser Thr Gln
    2570                2575                2580

Trp Leu Glu Ala Lys Glu Glu Ala Glu Gln Val Leu Gly Gln Ala
    2585                2590                2595

Arg Ala Lys Leu Glu Ser Trp Lys Glu Gly Pro Tyr Thr Val Asp
    2600                2605                2610

Ala Ile Gln Lys Lys Ile Thr Glu Thr Lys Gln Leu Ala Lys Asp
    2615                2620                2625

Leu Arg Gln Trp Gln Thr Asn Val Asp Val Ala Asn Asp Leu Ala
    2630                2635                2640

Leu Lys Leu Leu Arg Asp Tyr Ser Ala Asp Asp Thr Arg Lys Val
```

-continued

```
            2645                2650                2655
His Met Ile Thr Glu Asn Ile Asn Ala Ser Trp Arg Ser Ile His
        2660                2665                2670
Lys Arg Val Ser Glu Arg Glu Ala Ala Leu Glu Glu Thr His Arg
        2675                2680                2685
Leu Leu Gln Gln Phe Pro Leu Asp Leu Glu Lys Phe Leu Ala Trp
        2690                2695                2700
Leu Thr Glu Ala Glu Thr Thr Ala Asn Val Leu Gln Asp Ala Thr
        2705                2710                2715
Arg Lys Glu Arg Leu Leu Glu Asp Ser Lys Gly Val Lys Glu Leu
        2720                2725                2730
Met Lys Gln Trp Gln Asp Leu Gln Gly Glu Ile Glu Ala His Thr
        2735                2740                2745
Asp Val Tyr His Asn Leu Asp Glu Asn Ser Gln Lys Ile Leu Arg
        2750                2755                2760
Ser Leu Glu Gly Ser Asp Asp Ala Val Leu Leu Gln Arg Arg Leu
        2765                2770                2775
Asp Asn Met Asn Phe Lys Trp Ser Glu Leu Arg Lys Lys Ser Leu
        2780                2785                2790
Asn Ile Arg Ser His Leu Glu Ala Ser Ser Asp Gln Trp Lys Arg
        2795                2800                2805
Leu His Leu Ser Leu Gln Glu Leu Leu Val Trp Leu Gln Leu Lys
        2810                2815                2820
Asp Asp Glu Leu Ser Arg Gln Ala Pro Ile Gly Gly Asp Phe Pro
        2825                2830                2835
Ala Val Gln Lys Gln Asn Asp Val His Arg Ala Phe Lys Arg Glu
        2840                2845                2850
Leu Lys Thr Lys Glu Pro Val Ile Met Ser Thr Leu Glu Thr Val
        2855                2860                2865
Arg Ile Phe Leu Thr Glu Gln Pro Leu Glu Gly Leu Glu Lys Leu
        2870                2875                2880
Tyr Gln Glu Pro Arg Glu Leu Pro Pro Glu Glu Arg Ala Gln Asn
        2885                2890                2895
Val Thr Arg Leu Leu Arg Lys Gln Ala Glu Glu Val Asn Thr Glu
        2900                2905                2910
Trp Glu Lys Leu Asn Leu His Ser Ala Asp Trp Gln Arg Lys Ile
        2915                2920                2925
Asp Glu Thr Leu Glu Arg Leu Gln Glu Leu Gln Glu Ala Thr Asp
        2930                2935                2940
Glu Leu Asp Leu Lys Leu Arg Gln Ala Glu Val Ile Lys Gly Ser
        2945                2950                2955
Trp Gln Pro Val Gly Asp Leu Leu Ile Asp Ser Leu Gln Asp His
        2960                2965                2970
Leu Glu Lys Val Lys Ala Leu Arg Gly Glu Ile Ala Pro Leu Lys
        2975                2980                2985
Glu Asn Val Ser His Val Asn Asp Leu Ala Arg Gln Leu Thr Thr
        2990                2995                3000
Leu Gly Ile Gln Leu Ser Pro Tyr Asn Leu Ser Thr Leu Glu Asp
        3005                3010                3015
Leu Asn Thr Arg Trp Lys Leu Leu Gln Val Ala Val Glu Asp Arg
        3020                3025                3030
Val Arg Gln Leu His Glu Ala His Arg Asp Phe Gly Pro Ala Ser
        3035                3040                3045
```

-continued

```
Gln His Phe Leu Ser Thr Ser Val Gln Gly Pro Trp Glu Arg Ala
    3050            3055            3060

Ile Ser Pro Asn Lys Val Pro Tyr Tyr Ile Asn His Glu Thr Gln
    3065            3070            3075

Thr Thr Cys Trp Asp His Pro Lys Met Thr Glu Leu Tyr Gln Ser
    3080            3085            3090

Leu Ala Asp Leu Asn Asn Val Arg Phe Ser Ala Tyr Arg Thr Ala
    3095            3100            3105

Met Lys Leu Arg Arg Leu Gln Lys Ala Leu Cys Leu Asp Leu Leu
    3110            3115            3120

Ser Leu Ser Ala Ala Cys Asp Ala Leu Asp Gln His Asn Leu Lys
    3125            3130            3135

Gln Asn Asp Gln Pro Met Asp Ile Leu Gln Ile Ile Asn Cys Leu
    3140            3145            3150

Thr Thr Ile Tyr Asp Arg Leu Glu Gln Glu His Asn Asn Leu Val
    3155            3160            3165

Asn Val Pro Leu Cys Val Asp Met Cys Leu Asn Trp Leu Leu Asn
    3170            3175            3180

Val Tyr Asp Thr Gly Arg Thr Gly Arg Ile Arg Val Leu Ser Phe
    3185            3190            3195

Lys Thr Gly Ile Ile Ser Leu Cys Lys Ala His Leu Glu Asp Lys
    3200            3205            3210

Tyr Arg Tyr Leu Phe Lys Gln Val Ala Ser Ser Thr Gly Phe Cys
    3215            3220            3225

Asp Gln Arg Arg Leu Gly Leu Leu Leu His Asp Ser Ile Gln Ile
    3230            3235            3240

Pro Arg Gln Leu Gly Glu Val Ala Ser Phe Gly Gly Ser Asn Ile
    3245            3250            3255

Glu Pro Ser Val Arg Ser Cys Phe Gln Phe Ala Asn Asn Lys Pro
    3260            3265            3270

Glu Ile Glu Ala Ala Leu Phe Leu Asp Trp Met Arg Leu Glu Pro
    3275            3280            3285

Gln Ser Met Val Trp Leu Pro Val Leu His Arg Val Ala Ala Ala
    3290            3295            3300

Glu Thr Ala Lys His Gln Ala Lys Cys Asn Ile Cys Lys Glu Cys
    3305            3310            3315

Pro Ile Ile Gly Phe Arg Tyr Arg Ser Leu Lys His Phe Asn Tyr
    3320            3325            3330

Asp Ile Cys Gln Ser Cys Phe Phe Ser Gly Arg Val Ala Lys Gly
    3335            3340            3345

His Lys Met His Tyr Pro Met Val Glu Tyr Cys Thr Pro Thr Thr
    3350            3355            3360

Ser Gly Glu Asp Val Arg Asp Phe Ala Lys Val Leu Lys Asn Lys
    3365            3370            3375

Phe Arg Thr Lys Arg Tyr Phe Ala Lys His Pro Arg Met Gly Tyr
    3380            3385            3390

Leu Pro Val Gln Thr Val Leu Glu Gly Asp Asn Met Glu Thr Pro
    3395            3400            3405

Val Thr Leu Ile Asn Phe Trp Pro Val Asp Ser Ala Pro Ala Ser
    3410            3415            3420

Ser Pro Gln Leu Ser His Asp Asp Thr His Ser Arg Ile Glu His
    3425            3430            3435
```

| | | | | | | | | | | |
|---|---|---|---|---|---|---|---|---|---|---|
|Tyr|Ala|Ser|Arg|Leu|Ala|Glu|Met|Glu|Asn|Ser|Asn|Gly|Ser|Tyr|
| |3440| | | |3445| | | |3450| |

Leu Asn Asp Ser Ile Ser Pro Asn Glu Ser Ile Asp Asp Glu His
  3455             3460             3465

Leu Leu Ile Gln His Tyr Cys Gln Ser Leu Asn Gln Asp Ser Pro
  3470             3475             3480

Leu Ser Gln Pro Arg Ser Pro Ala Gln Ile Leu Ile Ser Leu Glu
  3485             3490             3495

Ser Glu Glu Arg Gly Glu Leu Glu Arg Ile Leu Ala Asp Leu Glu
  3500             3505             3510

Glu Glu Asn Arg Asn Leu Gln Ala Glu Tyr Asp Arg Leu Lys Gln
  3515             3520             3525

Gln His Glu His Lys Gly Leu Ser Pro Leu Pro Ser Pro Pro Glu
  3530             3535             3540

Met Met Pro Thr Ser Pro Gln Ser Pro Arg Asp Ala Glu Leu Ile
  3545             3550             3555

Ala Glu Ala Lys Leu Leu Arg Gln His Lys Gly Arg Leu Glu Ala
  3560             3565             3570

Arg Met Gln Ile Leu Glu Asp His Asn Lys Gln Leu Glu Ser Gln
  3575             3580             3585

Leu His Arg Leu Arg Gln Leu Leu Glu Gln Pro Gln Ala Glu Ala
  3590             3595             3600

Lys Val Asn Gly Thr Thr Val Ser Ser Pro Ser Thr Ser Leu Gln
  3605             3610             3615

Arg Ser Asp Ser Ser Gln Pro Met Leu Leu Arg Val Val Gly Ser
  3620             3625             3630

Gln Thr Ser Asp Ser Met Gly Glu Glu Asp Leu Leu Ser Pro Pro
  3635             3640             3645

Gln Asp Thr Ser Thr Gly Leu Glu Glu Val Met Glu Gln Leu Asn
  3650             3655             3660

Asn Ser Phe Pro Ser Ser Arg Gly Arg Asn Thr Pro Gly Lys Pro
  3665             3670             3675

Met Arg Glu Asp Thr Met
  3680

<210> SEQ ID NO 9
<211> LENGTH: 53
<212> TYPE: DNA
<213> ORGANISM: artificial
<220> FEATURE:
<223> OTHER INFORMATION: primer

<400> SEQUENCE: 9
ccgcgggtac caggatccgt cgacatcgat ccaccatggc caagtatgga gaa         53

<210> SEQ ID NO 10
<211> LENGTH: 27
<212> TYPE: DNA
<213> ORGANISM: artificial
<220> FEATURE:
<223> OTHER INFORMATION: primer

<400> SEQUENCE: 10
gtcgacagga atctgtctct tctttgg                                      27

<210> SEQ ID NO 11
<211> LENGTH: 40
<212> TYPE: DNA

-continued

```
<213> ORGANISM: artificial
<220> FEATURE:
<223> OTHER INFORMATION: primer

<400> SEQUENCE: 11
ttaaggatcc tcgagttttt caagtctcta agttgtcacc                    40

<210> SEQ ID NO 12
<211> LENGTH: 24
<212> TYPE: DNA
<213> ORGANISM: artificial
<220> FEATURE:
<223> OTHER INFORMATION: primer

<400> SEQUENCE: 12
gtcgacctgg agaagctcag agac                                     24
```

MICROUTROPHIN AND USES THEREOF

CROSS-REFERENCE TO RELATED APPLICATIONS

This is a national stage application under 35 U.S.C. 371 of PCT/US05/0011768, filed Jan. 21, 2005, which claims the benefit under 35 U.S.C. 119(e) of the priority of U.S. Patent Application No. 60/538,877 filed Jan. 23, 2004.

STATEMENT OF FEDERALLY SPONSORED RESEARCH

This invention was made with government support under grant No. 5R01NS042874 and awarded by the National Institutes of Health. The government may have certain rights in this invention.

BACKGROUND OF THE INVENTION

The present invention relates to the use of a microutrophin coding sequence in the treatment of muscular dystrophy.

Duchenne Muscular Dystrophy (DMD) is caused by a deficiency of the muscle cytoskeletal protein known as dystrophin. Dystrophin is a member of the spectrin superfamily of proteins and as such is distantly related to spectrin and alpha-actinin. Dystrophin is most closely related to the protein utrophin. The genes for these two proteins have nearly identical intron/exon structures, and the proteins are 50+% homologous at the amino acid level. Dystrophin is expressed throughout the entire length of the skeletal muscle fiber while utrophin is normally expressed only at the neuromuscular junction. Most cases of DMD result from sporadic deletions of the X chromosomal dystrophin gene. The destruction of the dystrophin open reading frame by these mutations suggests that therapies that genetically reconstitute dystrophin expression will elicit a cellular immune response against the fibers in which the protein is synthesized.

In the years following the initial discovery of utrophin, the technologies for targeted gene ablation in mice facilitated a formal genetic analysis of gene complementation. In the transgenic mouse in which the expression of utrophin is dictated by a muscle-specific promoter, utrophin can complement the physiological role of dystrophin.

Tinsley and Davies, U.S. Pat. No. 6,518,413, describe the expression of a polypeptide with utrophin function from a nucleic acid sequence for use in treatment of muscular dystrophy. This group designed a truncated protein modeled on a natural mutation identified in a mild Becker muscular dystrophy patient. However, while the constructs provide some amelioration of symptoms, they are not optimal in terms of size, permissible delivery routes, or therapeutic outcome.

More recently, X. Xiao, US Patent Application Publn No. US 2003/0171312 A1 and J. Chamberlain, et al, US Patent Application Publn No. US 2003/0216332 A1, have described mini-dystrophin genes for use in treating muscular dystrophies. In the case of US 2003/0171312 A1, the dystrophin mini-gene may contain regions of the utrophin gene.

What is needed is an improved method of treating muscular dystrophies.

BRIEF DESCRIPTION OF THE DRAWINGS

FIGS. 1A to 1N provide the sequences of a canine microutrophin cDNA of the invention [nucleotides 12-3497 of SEQ ID NO:1] in alignment with a human microutrophin coding sequences of the invention [SEQ ID NO: 6] and a mouse microutrophin coding sequence of the invention [SEQ ID NO: 7].

FIGS. 2A to 2E provide the sequences of a canine microutrophin of the invention [SEQ ID NO:2] in alignment with a human microutrophin of the invention [SEQ ID NO: 4] and a mouse microutrophin of the invention [SEQ ID NO: 5].

FIG. 3A to 3K provide an alignment of the human utrophin protein [SEQ ID NO:3] and the human dystrophin protein [SEQ ID NO:8]. The repeats and hinge regions are marked with respect to the utrophin protein above the sequence and for the dystrophin protein below the sequence.

SUMMARY OF THE INVENTION

Figure 3A:
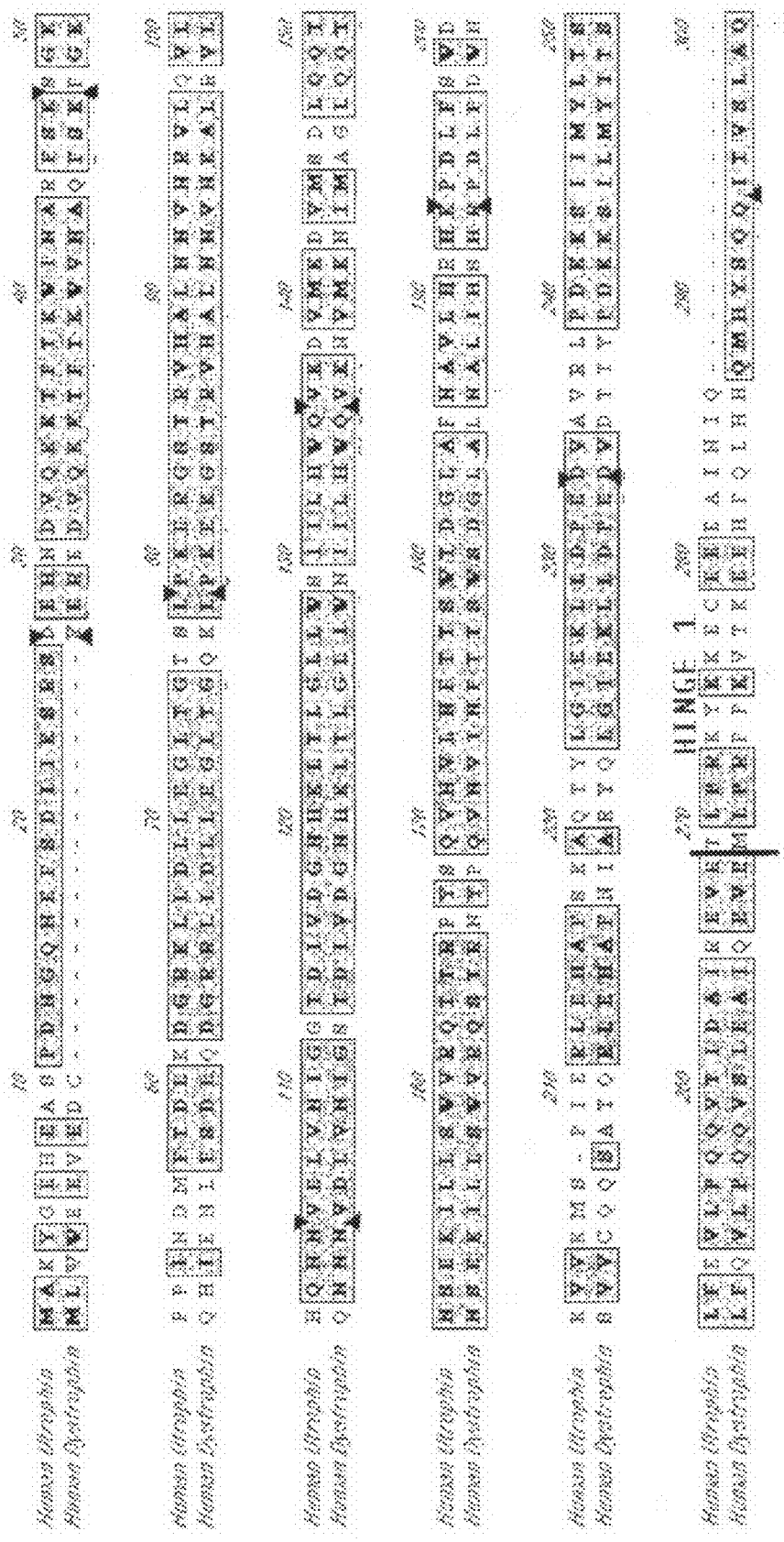

In one aspect, the present invention provides a vector comprising a microutrophin cassette useful in a medicament for treatment of muscular disorders, including muscular dystrophy.

In another aspect, the invention provides a pharmaceutical composition comprising the vector comprising the microutrophin cassette.

In yet another aspect, the invention provides a method of treating muscular dystrophies using microutrophin.

In still another aspect, the invention provides the use of a vector comprising a microutrophin cassette in the preparation of a medicament for treatment of muscular dystrophies.

Still other aspects and advantages of the invention will be apparent from the following detailed description of the invention.

DETAILED DESCRIPTION OF THE INVENTION

The present invention provides microutrophin useful in treatment of muscle wasting disorders characterized by dystrophic pathology and symptoms. The severe muscle wasting disorders include Duchenne muscular dystrophy (DMD) and the less debilitating Becker muscular dystrophy. The invention further provides pharmaceutical compositions, medicaments, and methods of use thereof, for treatment of such disorders.

Without wishing to be bound by theory, the inventors believe that the present invention is advantageous over prior dystrophin-based therapies, because such therapies are anticipated to cause an autoimmune response in subjects lacking the ability to express a functional native dystrophin gene. Further, the inventors believe that the present invention is advantageous over the previously described utrophin-based constructs of Tinsley and Davies, due to its design and the improved methods for delivery described herein.

The term "muscle cell" or "tissue" refers to a cell or group of cells derived from muscle, including but not limited to cells and tissue derived from skeletal muscle, cardiac muscle, smooth muscle, e.g., from the digestive tract, urinary bladder and blood vessels. The constructs of the invention can be delivered in vitro or in vivo, depending upon the application. Thus, for example, an isolated cardiomyocyte would constitute a "muscle cell" for purposes of the present invention, as would a muscle cell as it exists in muscle tissue present in a subject. The term also encompasses both differentiated and nondifferentiated muscle cells, such as myocytes, myotubes, myoblasts, cardiomyocytes and cardiomyoblasts, and progenitor cells, for example, the muscle derived stem cells or the bone marrow derived stem cells that can become muscle cells after differentiation.

The "microutrophin" of the invention is a utrophin polypeptide having a functional portion of the "actinin-binding domain" of about 270 amino acids relative to the human utrophin which is located within the N-terminal utrophin region, at least functional portions of the proline-rich hinge regions 1 and 4 (H1) and (H4), and a portion of the C-terminal utrophin protein. The microutrophin contains internal deletions in the central rod repeat domains and a truncation in the C-terminal region downstream, but retains the proper phasing (i.e., conformation) to retain the desired biological function of utrophin. This construct of the invention is described in detail below.

Utrophin shows substantial homology to dystrophin, with significant divergence occurring in the rod domain, where utrophin lacks repeats 15 and 19 and two hinge regions (See e.g., Love et al., *Nature* 339:55 [1989]; Winder et al., *FEBS Lett.*, 369:27 [1995]). Human utrophin contains 22 spectrin-like repeats and two hinge regions. See, e.g., Genbank® accession number X69086 and GenBank® accession number AL357149, which provides full-length human UTRN gene for utrophin and encoded protein. Homologs of utrophin have been identified in a variety of organisms, including mouse (Genbank® accession number Y12229), rat (Genbank® accession number AJ002967), and dog (GenBank® accession number NW-139836). The nucleic acid sequence of these or additional homologs can be compared to the nucleic acid sequence of human utrophin using any suitable methods.

The "microutrophin" polypeptide provided in SEQ ID NO:2 and described in the examples is an artificial polypeptide containing an internal deletion and a C-terminal deletion, with respect to the native utrophin polypeptide. More particularly, the microutrophin polypeptide of FIG. 2 contains the N-terminal region of utrophin, hinge 1 (H1), and hinge 2 (H2), an internal deletion from Repeat 4 through Repeat 21, and, Repeat 22 through the C-terminal region until about Exon 63. The C-terminal region from Exon 63 through the native C-terminal region is deleted. Thus, the N-terminal utrophin amino acids through hinge 2 (H2) are fused to amino acids of Repeat 22 through the C-terminal region of Exon 62. The coding sequences for this polypeptide are provided in SEQ ID NO:1.

Figure 3B:
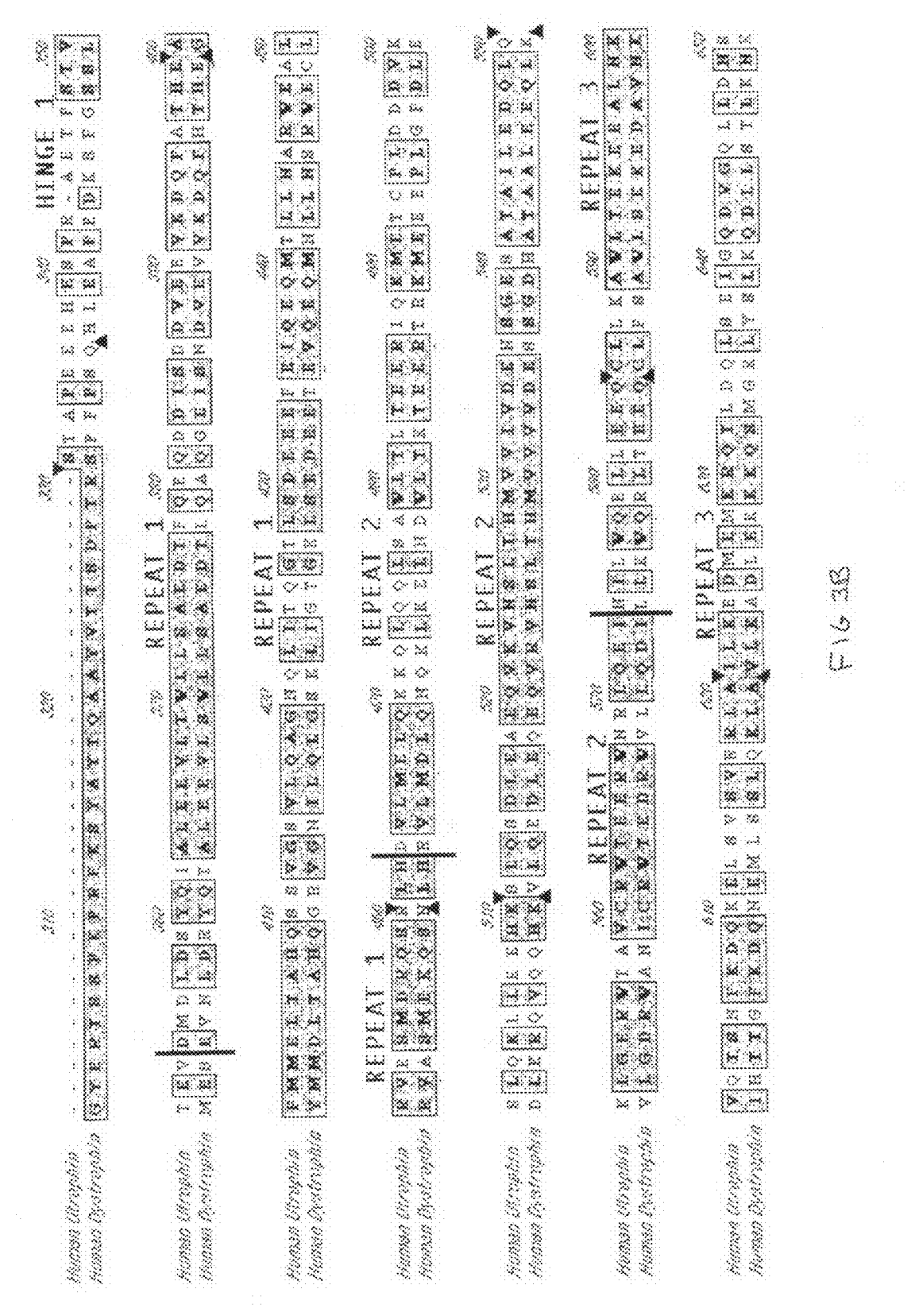
Figure 3C:
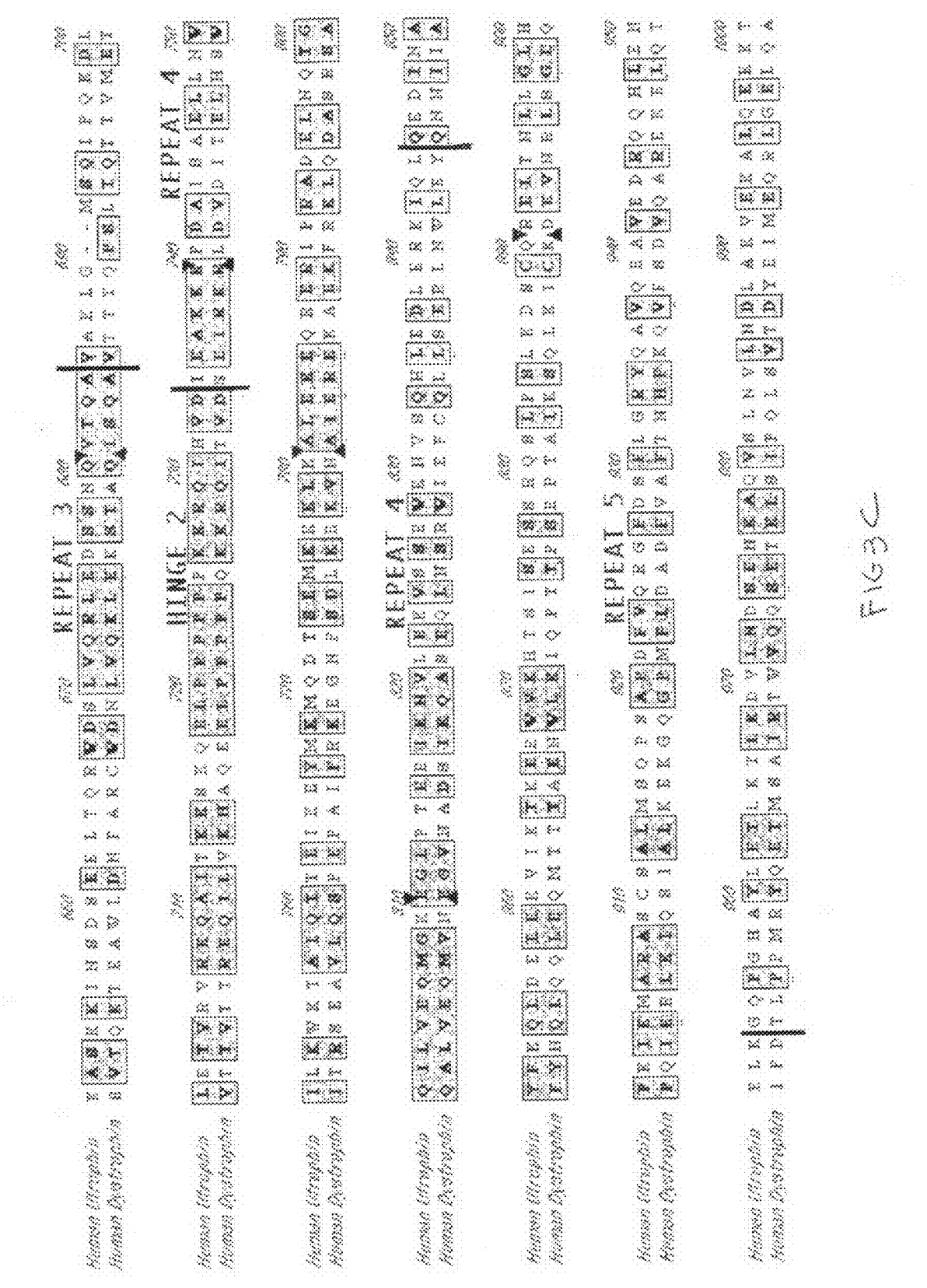
Figure 3D:
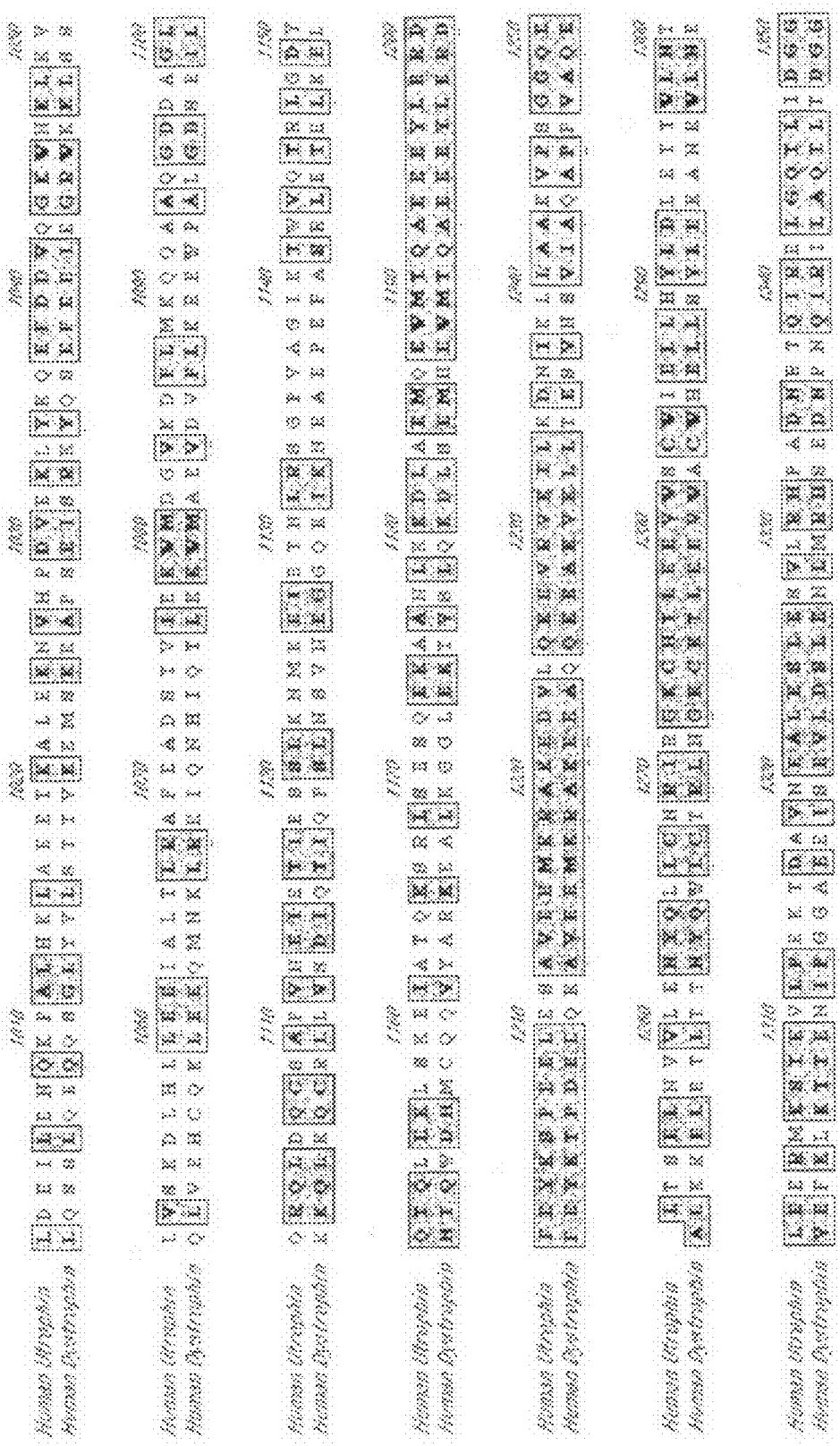
Figure 3E:
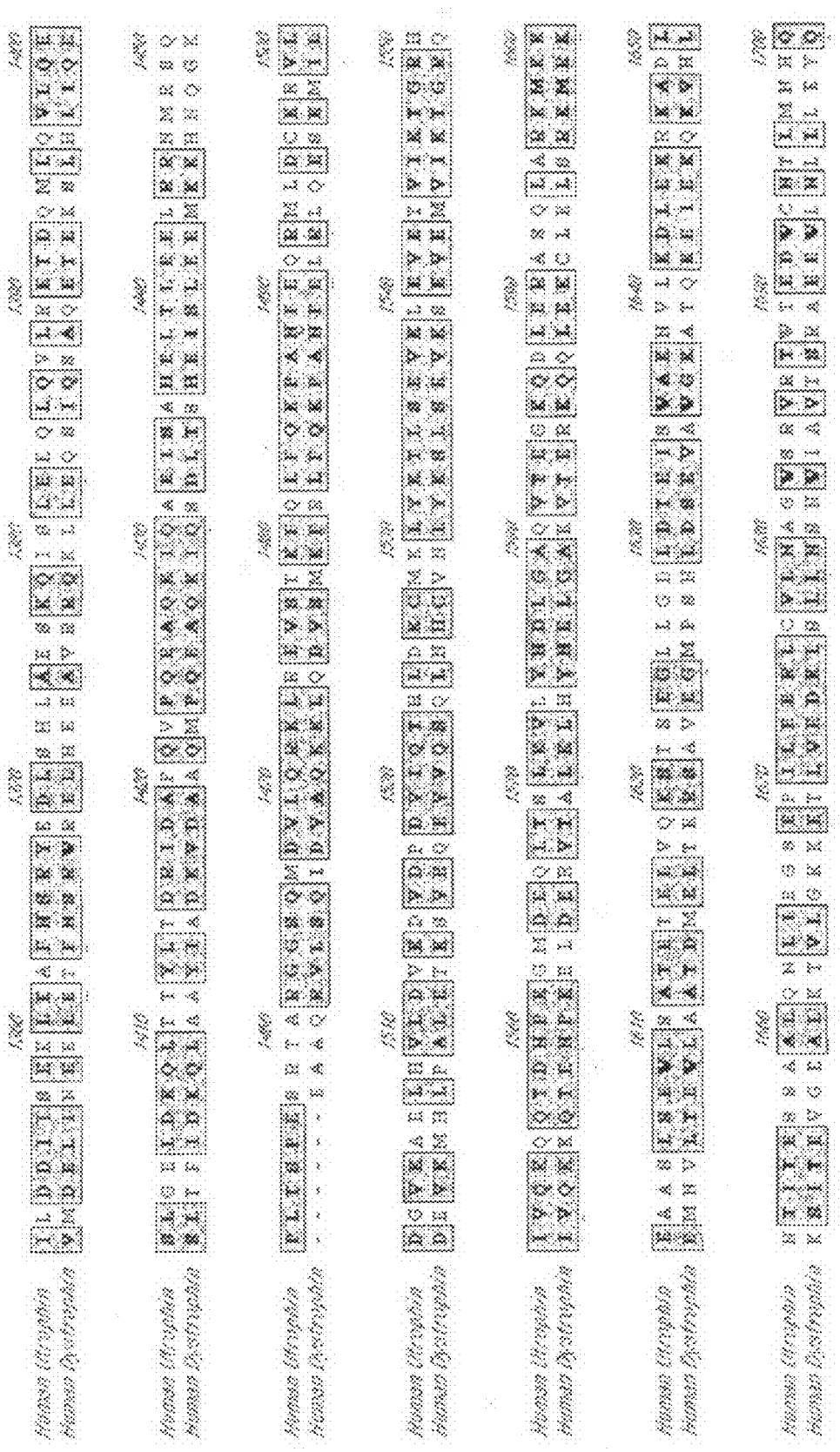
Figure 3F:
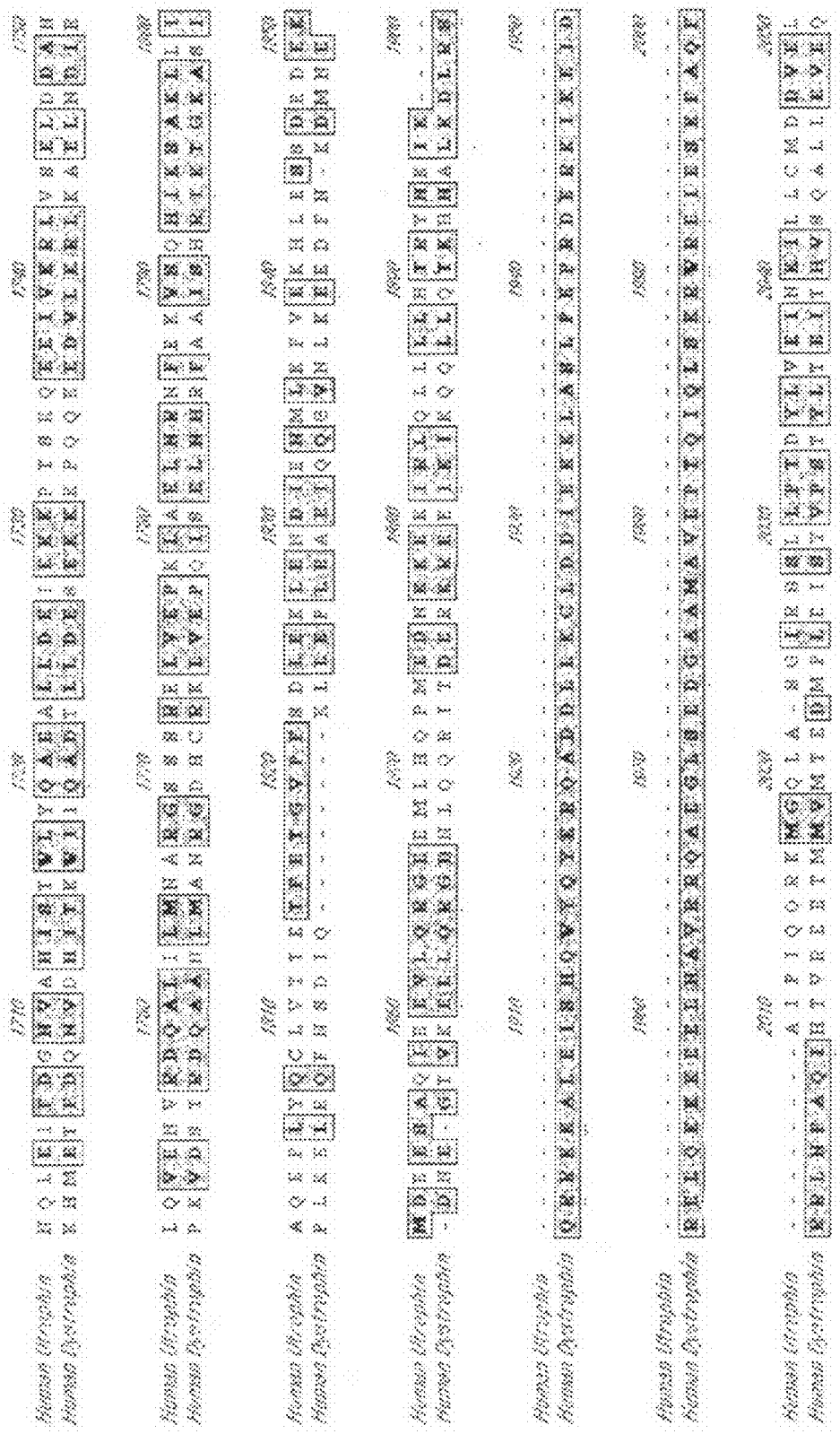
Figure 3G:
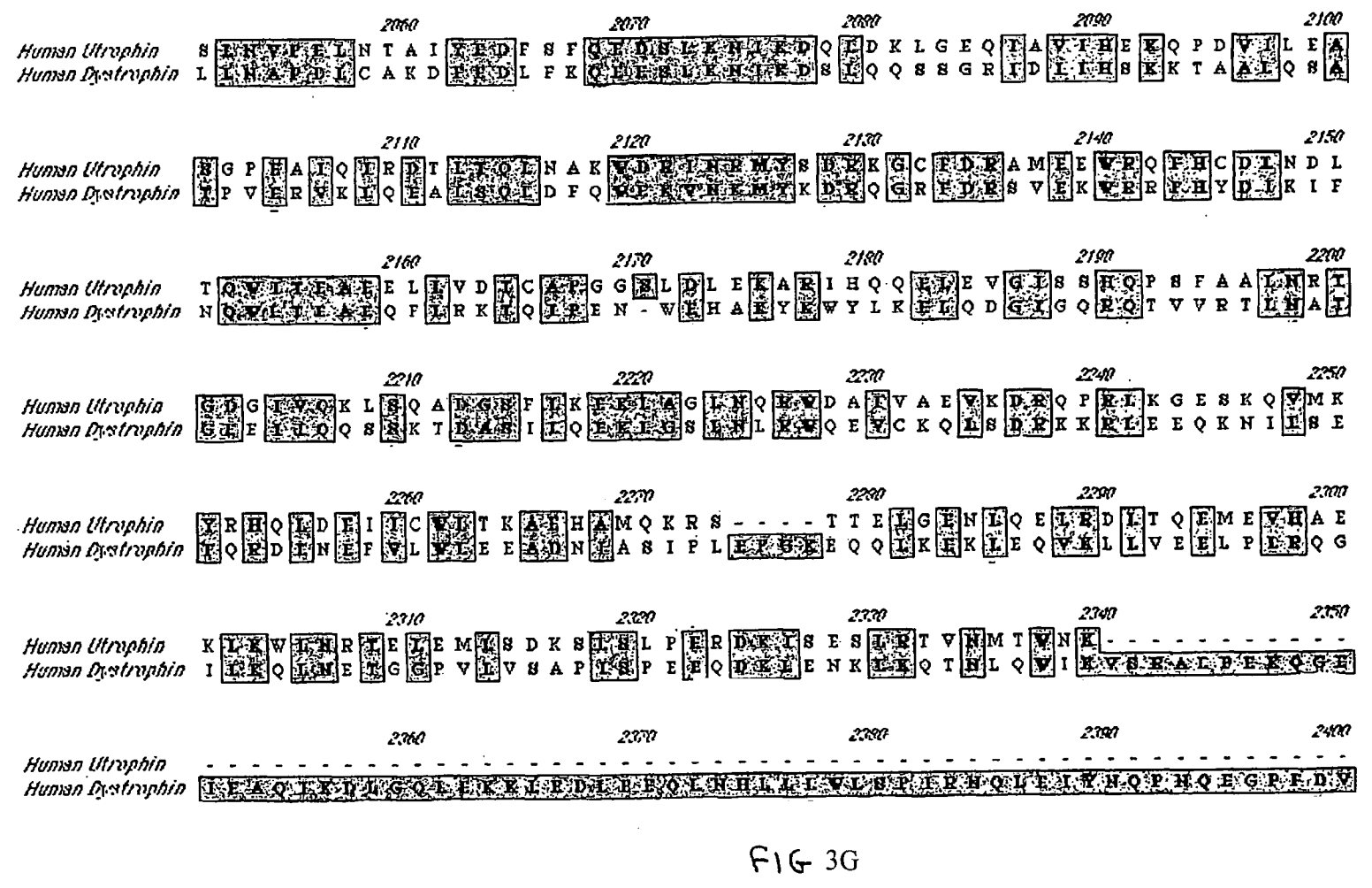
Figure 3J:
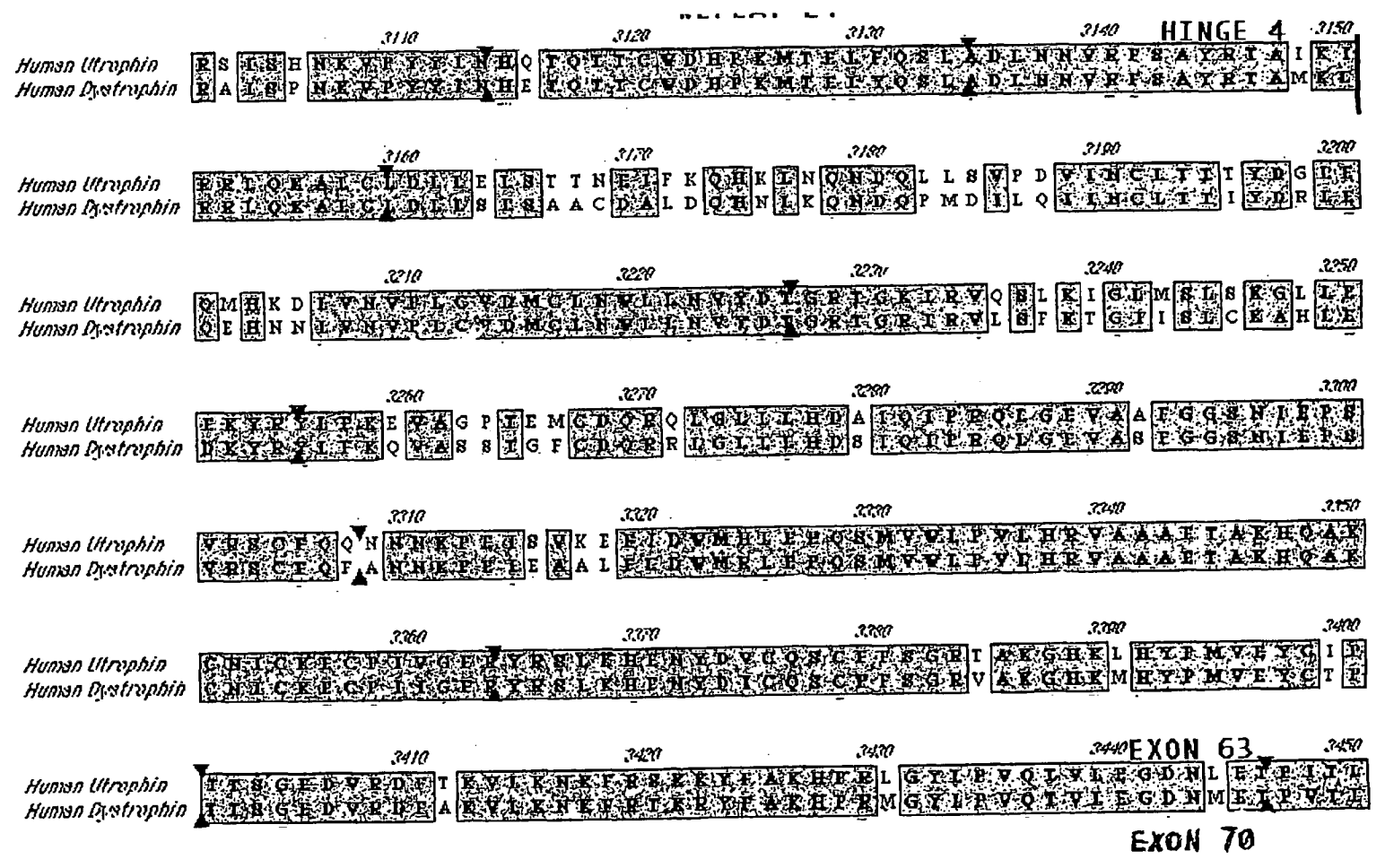
Figure 3K:
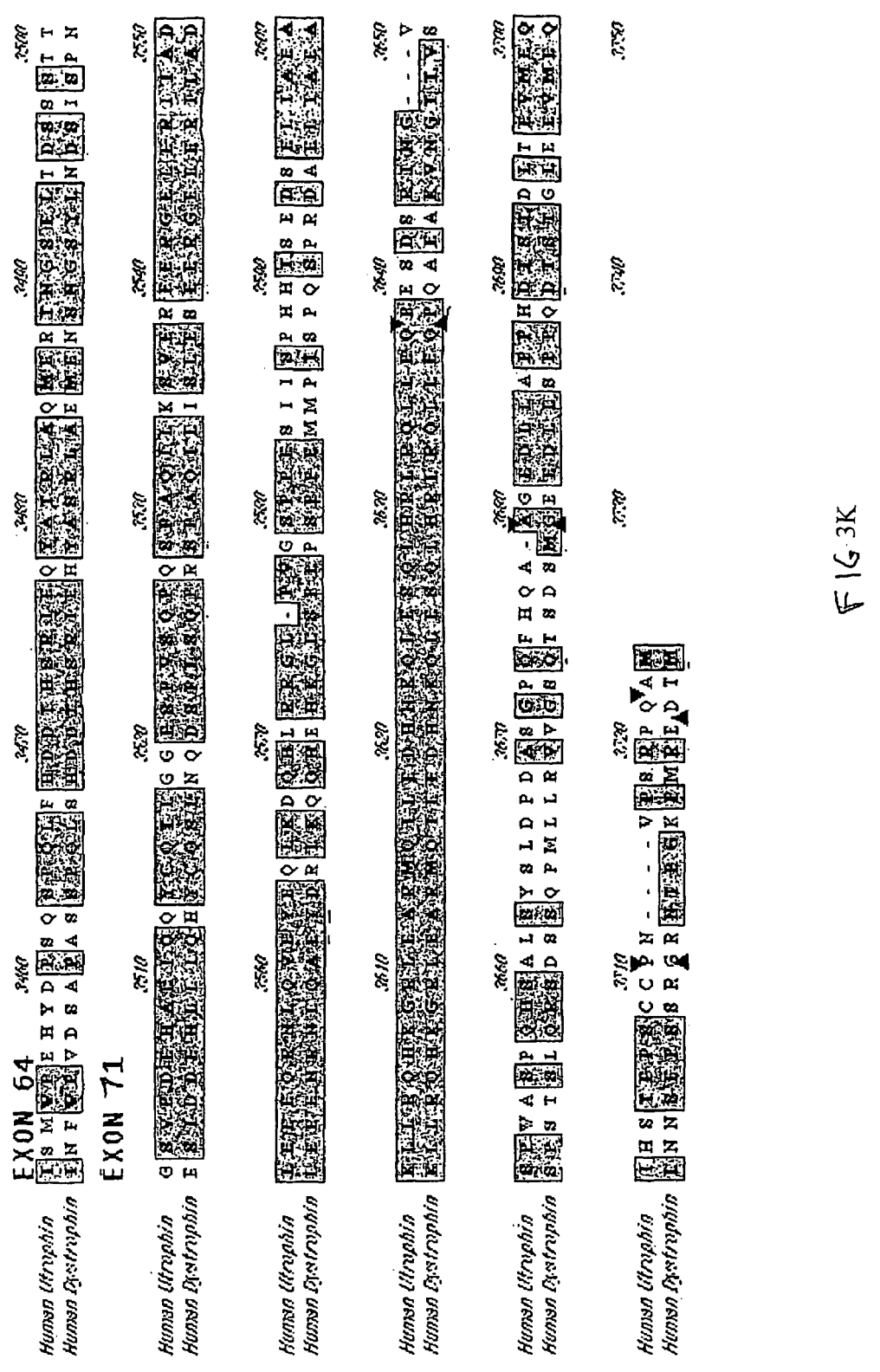

However, the microutrophin of the invention is not limited to this precise construct. Desirably, a microutrophin polypeptide contains amino acids from the N-terminal region of utrophin, at least two of the hinge regions, and all or a portion of the C-terminal region. In one embodiment, the N-terminal region of utrophin comprises a polypeptide from the N-terminus to about the hinge region (e.g., about amino acid 1 to 268 based on the aligned human utrophin sequence in FIG. 3 [SEQ ID NO:3].); however, shorter or longer fragments of the utrophin sequence N-terminal to the hinge region may be selected. For example, 1 to 10, 1 to 5, 2, 3 or 4 of the first amino acids of the N-terminal sequences may be deleted. In one embodiment, the microutrophin is deleted of all or a fragment of hinge region 3. In another embodiment, the microutrophin is deleted of a fragment of hinge region 4. Suitably, the deletions are selected such that they permit proper conformational alignment of the utrophin protein, and particularly, retain the critical triple helices formed by the utrophin polypeptide. Preferably, the C-terminal cysteine-rich (CR) domain is truncated from a location at about Exon 63 [about amino acid 3346 of SEQ ID NO: 3] through the end of the utrophin protein. In another embodiment, a longer portion of the C-terminal region, e.g., about Exon 64-end, about Exon 65-end, about Exon 66-end, or more, can be retained. In one embodiment, the microutrophin comprises the N-terminal region of utrophin, at least hinges H1 and hinge 4 (H4) of utrophin gene, and at least four of the central rod repeats of the utrophin genes.

Preferably, for use in human subjects, human microutrophin sequences are selected in order to minimize any immune response. Similarly, for a dog, canine sequences are preferably selected. The appropriate locations of the N-terminal, C-terminal, and internal deletions described herein in the context of the human and canine sequences can be readily determined for other utrophin homologs, by preparing an alignment and comparison to the sequences of human utrophin using any suitable methods.

The sequences encoding the microutrophin polypeptide, or the fragments thereof which are fused in frame to generate the microutrophin, can be obtained by conventional techniques. For the experiments described herein, the utrophin sequences were obtained by reverse transcriptase (RT) polymerase chain reaction (PCR) techniques from tissue from a dystrophic animal. Alternatively, utrophin sequences may be obtained from other suitable sources, or suitable fragments may be prepared using synthetic methods. The source of the microutrophin sequences is not a limitation of the present invention.

The term "microutrophin gene" or "microutrophin coding sequences" refers to a nucleic acid molecule containing sequences encoding the microutrophin constructs described herein. These sequences may be those encoding the native utrophin fragments for the constructed microutrophin polypeptide. Alternatively, the microutrophin gene may contain a modified N-terminal domain in which DNA sequences surrounding the original protein translation initiation codon ATG are modified. The N-terminus of the microutrophin gene may be modified to improve expression efficiency without affecting the functionality of the gene product. For example, the original, sequence surrounding the translation initiation ATG codon of the utrophin gene may be substituted by the Kozak sequence to increase the efficiency of protein synthesis. In one embodiment of the current invention, the three nucleotides upstream of the coding sequence may be changed from "AAA" to "CCA" and the fourth nucleotide in the coding sequence may be changed from "C" to "G". The modified sequences are useful to enhance the yield and/or purification of microutrophin protein synthesis.

The nucleic acid sequences encoding microutrophin can be generated using techniques known to those of skill in the art and engineered into an appropriate expression cassette under the control of regulatory sequences which direct its expression in a cell. Suitably, the microutrophin expression cassette is inserted into a vector for targeting to a desired host cell and/or into a subject. The term "expression cassette" refers to a construct of genetic material that contains coding sequences and enough regulatory information to direct proper transcription and translation of the coding sequences in a recipient cell.

The microutrophin expression cassette may be introduced into a mammalian subject using a variety of methods. It may be delivered as a naked DNA with or without hydrodynamic-based or electroporation-based procedures. The microutrophin expression cassette can also be delivered using a suitable vector. A gene transfer "vector" refers to any agent, such as a plasmid, phage, transposon, cosmid, chromosome, liposome, DNA-viral conjugates, RNA/DNA oligonucleotides, virus, bacteria, etc., which is capable of transferring gene sequences into cells. Thus, the term includes cloning and expression vehicles, as well as non-viral and viral vectors.

Non-viral vectors such as liposomes or virus-liposome complexes, or with viral vectors such as adenovirus, HSV, baculovirus, retrovirus, lentivirus, and preferably AAV. Expression of the microutrophin minigenes may be controlled by a number of regulatory elements, including but not limited to, AAV inverted terminal repeat (ITR), retrovirus long terminal repeat (LTR), cytomeglovirus (CMV) immediate early promoter and/or enhancer, CMV enhancer and chicken β-actin promoter (CB promoter), α-actin promoter, myosin promoter, muscle-specific creatine kinase (MCK) promoter and/or enhancer, and the like. In one embodiment, the muscle-specific promoters, including modified versions of the above promoters and the synthetic muscle promoters, may also be used.

Optionally, a vector is targeted to specific cells by linking a target molecule to the vector. A targeting molecule is any agent that is specific for a cell or tissue type of interest, including for example, a ligand, antibody, sugar, receptor, or other binding molecule. The invention is also intended to include such other forms of vectors which serve equivalent functions and which become known in the art subsequently hereto. The term "transduction" denotes the delivery of a DNA molecule to a recipient cell either in vivo or in vitro, via a replication-defective viral vector, such as via a recombinant AAV virion.

As used herein the term "regulatory sequences" pertains to sequences operably linked to the encoded gene product. In addition to the major elements identified above, the macromolecular complex (e.g., a vector) also includes conventional control elements that are operably linked to the transgene in a manner that permits its transcription, translation and/or expression in a cell transfected with the macromolecular complex.

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters that are native, constitutive, inducible and/or tissue-specific, are known in the art and may be utilized.

In one embodiment, the regulatory sequences are optimized for expression in the muscle and/or comprise tissue-specific promoters. For instance, if expression in skeletal muscle is desired, a promoter active in muscle can be used. These include the promoters from genes encoding skeletal β-actin, myosin light chain 2A, dystrophin, muscle creatine kinase, as well as synthetic muscle promoters with activities higher than naturally-occurring promoters (see Li et al., *Nat. Biotech.*, 17:241-245 (1999)). However, one of skill in the art can readily select a suitable constitutive, inducible, or regulated promoter.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, *Cell*, 41:521-530 (1985)], the SV40 promoter, the dihydrofolate reductase promoter, the β-actin promoter, the phosphoglycerol kinase (PGK) promoter, and the EF1 promoter [Invitrogen]. Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied compounds, include, the zinc-inducible sheep metallothionine (MT) promoter, the dexamethasone (Dex)-inducible mouse mammary tumor virus (MMTV) promoter, the T7 polymerase promoter system [International Patent Publication No. WO 98/10088]; the ecdysone insect promoter [No et al, *Proc. Natl. Acad. Sci. USA,* 93:3346-3351 (1996)], the tetracycline-repressible system [Gossen et al, *Proc. Natl. Acad. Sci. USA,* 89:5547-5551 (1992)], the tetracycline-inducible system [Gossen et al, *Science,* 268:1766-1769 (1995), see also Harvey et al, *Curr. Opin. Chem. Biol.,* 2:512-518 (1998)], the RU486-inducible system [Wang et al, *Nat. Biotech.,* 15:239-243 (1997) and Wang et al, *Gene Ther.,* 4:432-441 (1997)] and the rapamycin-inducible system [Magari et al, *J. Clin. Invest.,* 100:2865-2872 (1997)]. Other types of inducible promoters that may be useful in this context are those that are regulated by a specific physiological state, e.g., temperature, acute phase, a particular differentiation state of the cell, or in replicating cells only.

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

Methods for assembling and producing a variety of different vectors defined herein are known to those of skill in the art and have been described in textbooks and in the literature. See, e.g., Sambrook et al, Molecular cloning: A Laboratory Manual, Cold Spring Harbor Press, Cold Spring Harbor, N.Y. (2000). Production of the vector is not a limitation of the present invention.

An "AAV vector" refers to vectors derived from an adeno-associated virus serotype, including human AAV-1, AAV-2, AAV-3, AAV-4, AAV-5, AAV-6, avian AAV, ovian AAV, etc., AAV7 [International Patent Application No. PCT/US02/33629], AAV8 [International Patent Application No. PCT/US02/33629], human AAV9 [International Patent Application No. PCT/US04/028817], among others which have been described [G. Gao, et al., *J Virol.* 2004 June; 78(12):6381-8; G. Gao, et al, *Proc Natl Acad Sci USA.* 2003 May 13; 100 (10):6081-6. Epub 2003 Apr. 25], and to vectors derived from more than one AAV serotype (hybrid AAV vectors). For example, a hybrid AAV vector may contain DNA sequences derived from both AAV-1 and AAV-2. An AAV vector can have one or more of the AAV wild-type genes deleted in whole or part, preferably the rep and/or cap genes, but retain functional flanking ITR sequences. AAV vectors can be constructed using recombinant techniques that are known in the art to include one or more heterologous nucleotide sequences flanked on both ends (5' and 3') with functional AAV ITRs. In the practice of the invention, an AAV vector can include at least one AAV ITR and a suitable promoter sequence positioned upstream of the heterologous nucleotide sequence and at least one AAV ITR positioned downstream of the heterologous sequence.

A "recombinant AAV vector plasmid" refers to one type of recombinant AAV vector wherein the vector comprises a plasmid. As with AAV vectors in general, 5' and 3' ITRs flank the selected heterologous nucleotide sequence. AAV vectors can also include transcription sequences such as polyadenylation sites, as well as selectable markers or reporter genes, enhancer sequences, and other control elements which allow for the induction of transcription. Such control elements are described more fully below. In addition, an "AAV vector" can be stably introduced into a cell line or cell lines for the purpose of viral particle production. Such a cell line is usually termed as AAV packaging cell line.

As used herein, the term "recombinant AAV", "recombinant AAV particle" or "recombinant AAV virion" is defined as an infectious, replication-defective virus composed of an AAV protein shell encapsidating (i.e., surrounding with a protein coat) a heterologous nucleotide sequence, which in turn is flanked 5' and 3' by AAV ITRs. In this regard, single-stranded AAV nucleic acid molecules (either the sense/coding strand or the antisense/anticoding strand as those terms are generally defined) can be packaged into an AAV virion; both the sense and the antisense strands are equally infectious. When the recombinant AAV DNA is equal to or smaller than 50% of the full length viral genome (about 5,000 nucleotides), it can also be packaged as double-stranded hairpin-like DNA into AAV virion. Such virion is also fully infectious.

The term "recombinant AAV particle" or "recombinant AAV virion" also refers to a hybrid AAV particle in which the AAV protein shell and the encapsulated nucleotide sequence may be derived from AAVs of different serotype. For example, a hybrid AAV particle may contain AAV-1 capsid proteins and AAV-2 ITRs, or vice versa. It is also possible to create hybrid AAV capsid proteins using coding sequences from two or more AAV capsid genes. In addition, the capsid protein of a recombinant AAV may be manipulated by mutation, deletion, and/or insertion of amino acid sequence in order to modify the tropism of the recombinant AAV (Wu et al. J. Virol 74, 8635-47 [2000]; Girod et al. Nat Med 5, 1052-1056 [1999]).

A number of techniques for constructing recombinant AAV are known in the art. See, e.g., U.S. Pat. No. 5,173,414, Lebkowski et al. Mol Cell Biol 8, 3988-3996 [1988]; Carter B J, Current Opinion in Biotechnology 3, 533-539 [1992]; Muzyczka N, cited supra; and Zhou et al. J. Exp. Med. 179, 1867-1875 [1994]; Xiao et al. J. Virol. 72, 2224-32 [1998]; also, International Patent Appln No. PCT/US02/33629], AAV8 [International Patent Appln No. PCT/US02/33629], human AAV9 [International Patent Appln No. PCT/US04/028817], among others which have been described [G. Gao, et al., *J Virol.* 2004 June; 78(12):6381-8; G. Gao, et al, *Proc Natl Acad Sci USA.* 2003 May 13; 100(10):6081-6. Epub 2003 Apr. 25].

Other suitable vectors may be selected for targeting to a desired host cell including, e.g., adenovirus, retroviral, lentivirus, and plasmids. Suitable methods for constructing adenoviral [e.g., S. Roy, et al., Virology, 2004 Jul. 1; 324(2): 361-72; WO 03/046124], lentiviral [e.g., WO 01/83730; WO 99/61598; R. Zuffery et al, J. Virol., 72 (12):9873-9880 (December 1998); H. Miyoshi et al, J Virol, 72(10):8150-8157 (October 1998) and plasmid vectors [see, e.g., J. Sambrook, et al, "Molecular Cloning: A Laboratory Manual", Cold Spring Harbor Press, Cold Spring Harbor, N.Y. (2000)]have been described.

Any of the above-described vectors carrying the microutrophin expression cassette may be formulated for delivery to host cells or a subject according to published methods. The vector is mixed with a physiologically compatible carrier for administration to a human or non-human mammalian patient. Suitable carriers may be readily selected by one of skill in the art in view of the route(s) of delivery. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present invention.

Optionally, the compositions of the invention may contain, in addition to the vector and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The vectors are administered to a subject in an effective amount. By "subject" is meant any mammal, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered.

As used herein, the term "effective amount" refers to a level which brings about at least partially a desired therapeutic or prophylactic effect in a tissue targeted by the method of the present invention. The infection with an effective amount of the vector carrying genetic material of interest can then result in the modification of the cellular activities, e.g., a change in phenotype, in a tissue targeted by the method of the present invention.

Conventional and pharmaceutically acceptable routes of administration include, but are not limited to, direct delivery to the liver or lung, orally, intranasally, intratracheally, by inhalation, intravenously, intramuscularly, intraocularly, subcutaneously, intradermally, or by other routes of administration. Currently, intravenous and oral delivery routes are most desirable. However, other routes and combinations of different routes may be used, as desired.

Preferably, the constructs of the invention utilize promoters that direct expression in both skeletal and cardiac muscle. Such promoters may be constitutive promoters, examples of which are provided below. Alternatively, muscle specific promoters may be utilized. In one embodiment, the invention involves delivery of a microutrophin under the control of regulatory sequences comprising a promoter specific for skeletal muscle. In another embodiment, the invention involves delivery of a microutrophin under the control of regulatory sequences comprising a promoter specific for cardiac muscle. In still another embodiment, the invention involves delivery of a mixture of microutrophin vectors, one specifically targeting skeletal muscle and another specifically targeting cardiac muscle expression.

In one embodiment, delivery is accomplished by the global myocardial perfusion method described in International Patent Application No. PCT/US2004/030463. In another embodiment, delivery is accomplished by the gene transfer methods described in International Patent Application No. PCT/US2004/031322, filed Sep. 24, 2004. Briefly, this method involves transferring a microutrophin of the invention to muscle cells by exsanguinating a region of the subject's microvasculature and delivering the complex to this region under high hydrostatic pressure using a configuration of perfusion cannulae and balloon as required to protect heart and lung to protein the organs during perfusion. A balloon catheter having a balloon that extends substantially the full length of the aorta or vessel that is inserted into the subject is provided for use in the systemic delivery of vector. In still another embodiment, the invention provides for delivery via a perfusion circuit and surgical method is provided for delivering a substance to a subject's heart in situ during cardiopulmonary bypass surgery. The perfusion circuit defines a path for re-circulating a solution containing a macromolecular complex through a coronary circulation circuit through a subject's heart during a surgical procedure in which the substance is prevented from being delivered to the subject's other organs. [U.S. patent application Ser. No. 60/614,892.]

Dosages of the vector will depend primarily on factors such as the condition being treated, the age, weight and health of the patient, and may thus vary among patients. For example, a therapeutically effective human dosage of the vector is generally in the range of from about 1 ml to about 100 ml of solution containing concentrations of from about $1 \times 10^7$ to $1 \times 10^{16}$ genomes or particles vector. The dosage will be adjusted to balance the therapeutic benefit against any side effects and such dosages may vary depending upon the therapeutic application for which the recombinant vector is employed. The levels of expression of the transgene can be monitored to determine the frequency of dosage resulting in vectors, preferably AAV vectors containing the minigene. Optionally, dosage regimens similar to those described for therapeutic purposes may be utilized for immunization using the compositions of the invention.

Optionally, therapy with microutrophin can be combined with other therapies.

Expression of the microutrophin minigene may be detected by immunofluorescent staining and immunoblotting (Western blotting). Microutrophin therapy may be monitored by measuring missing DAP complexes on the myofiber plasma membrane, including the sarcoglycan complex which is typically not found in untreated dystrophic muscle due to the primary deficiency of dystrophin. Alternatively, microutrophin therapy can be monitored by assessing that muscle is protected from pathological phenotypes.

In one aspect, the invention provides a kit for use by a clinician or other personnel. Typically, such a kit will contain a microutrophin vector of the invention and, optionally, instructions for reconstitution and/or delivery thereof. In another embodiment, the kit will contain the microutrophin vector in a physiologically compatible saline solution and, optionally, instructions for dilution, and performing a method as described herein.

The kit of the invention may also contain a balloon catheter to facilitate somatic gene transfer as described [International Patent Application No. PCT/US2004/030463, or by the gene transfer methods described in International Patent Application No. PCT/US2004/031322, filed Sep. 24, 2004], oxygen-transporting agent and/or at least one disposable element of an extracorporeal circulatory support and oxygenation system. For example, at least one disposable element can be an oxygenator having a hollow body, a liquid inlet in fluid communication with the interior of the body, a liquid outlet in fluid communication with the interior of the body, a gas inlet for providing gas to the interior of a gas chamber, at least one gas-permeable membrane separating the gas chamber from the interior of the body, and a gas outlet for permitting gas to exit from the gas chamber, whereby gas exchange is enabled between a fluid in the interior of the body and a gas in the gas chamber. The oxygenator may be constructed as described in U.S. Pat. No. 6,177,403, wherein the gas-permeable membrane comprises PTFE tubing extending within at least a portion of the tube, and wherein the gas chamber comprises the interior of the PTFE tubing.

The following examples are illustrative of the invention. However, it will be understood that the invention is not limited to the following specified embodiments, or the methods or techniques for production or expression described therein.

EXAMPLE 1

Generation of Viral Vector containing Microutrophin Expression Cassette

To obtain the microutrophin, mRNA was extracted from frozen aliquot of canine muscle and reverse transcribed into cDNA using the RETROscript system (Ambion). The cDNA was used as template for PCR using primers for canine utrophin. The PCR products were analyzed on 1.2% agarose gel.

Two microutrophin fragments were made by PCR cloning using Taq polymerase (ROCHE) and canine cDNA as the template. The first fragment cDNA was amplified with the primers, 5' CCG CGG GTA CCA GGA TCC GTC GAC ATC GAT CCA CCA TGG CCA AGT ATG GAG AA (sense, SEQ ID NO: 9) and Hinge 2 (Sal), 5' GTC GAC AGG AAT CTG TCT CTT CTT TGG (antisense; SEQ ID NO: 10). The second fragment used the primers, 3' Exon70 TTA AGG ATC CTC GAG TTT TTC AAG TCT CTA AGT TGT CAC C, SEQ ID NO: 11; Rpt 24 (Sal) 5'-GTC GAC CTG GAG AAG CTC AGA GAC-3'; SEQ ID NO:12.

Two microutrophin fragments were then joined at a Sal I site to form the microutrophin cassette. PCR TOPO (Invitrogen) cloning vector according to manufacture's instruction.

The plasmid DNA was isolated and analyzed by restriction analysis to confirm the presence of the insert. The DNA was sequence to verify the presence of the gene. The microutrophin gene was isolated from the plasmid DNA (with ClaI and XhoI restriction sites) and cloned into an AAV vector plasmid containing a cytomegalovirus (CMV) promoter and the small poly (A) signal sequence to generate the viral vector AAV2/1-CMV microutrophin. The recombinant AAV serotype 2/1 was prepared by published methods [A. Auricchio et al, J Clin Invest. 110(40:499-504 (Aug. 15, 2002); W. Xiao et al, J Virol, 73:3994-4003 (1999); U.S. Pat. No. 6,759,237].

EXAMPLE 2

Expression of Functional Microutrophin

The mdx mouse (Bulfield et al. Proc. Natl. Acad. Sci. USA 81, 1189-1192 [1984]) is an animal model of DMD [purchased from Jackson Laboratory]. The genetic lesion in the mdx dystrophin gene is a nonsense mutation at base 3185 of the mRNA that causes premature termination of translation within exon 23. This nonsense mutation precludes synthesis of a functional protein. The mdx mouse model was used to assess the histological and western blot appearance of recombinant canine microutrophin.

Briefly, AAV2/1-microutrophin was into the right quadricep muscle of the mdx mice (intramuscular injection) with $1 \times 10^{12}$ GC particles of purified virus AAV microutrophin. Muscle samples were collected for examination at various time points (approximately 1 to 2 months) after vector injection.

Muscle cryosections were immunofluorescently stained with utrophin (N-terminus) mouse monoclonal antibody (Vector Labs) and donkey anti-mouse FITC (Jackson ImmunoResearch). Slides were examined with a Nikon microscope.

Protein expression was observed in the neuromuscular junctions and in low level staining of sarcolemma and vessel walls in mdx mice. Molecular weights are 133 kd for the microutrophin.

The construct will be further assessed in a German Short haired Pointer dog, because of its complete deletion of the dystrophin coding sequence (SJ Schatzberg, et al, Neuromuscul Disord. 1999 July; 9(5):289-95.).

All documents and GenBank® citations identified herein are incorporated by reference. Numerous modifications to, and variations of, the specific embodiments described herein will be readily apparent to one of skill in the art. The appended claims are intended to be construed to include all such embodiments and equivalent variations.

The invention claimed is:

1. A vector comprising a nucleic acid sequence encoding microutrophin under the control of regulatory sequences which direct expression of the microutrophin in a host cell, wherein the microutrophin comprises an N-terminal region of utrophin comprising hinge region 1, at least four utrophin central rod repeats, an internal deletion from repeat 4 through repeat 21, hinge region 4, and a deletion in the C-terminal utrophin region relative to human utrophin.

2. The vector according to claim 1 wherein said vector is selected from the group consisting of an adeno-associated viral vector and a plasmid vector.

3. The vector according to claim 1 wherein the microutrophin comprises a C-terminal deletion from exon 63 through the C-terminal amino acid of the native utrophin protein.

4. The vector according to claim 1 wherein the microutrophin comprises the N-terminal sequences of utrophin through at least two hinge regions, and a C-terminal region from repeat 22 through exon 63.

5. The vector according to claim 1 wherein the regulatory sequences comprise a constitutive promoter.

6. The vector according to claim 1 wherein the regulatory sequences comprise a muscle-specific promoter.

7. A pharmaceutical composition comprising a vector according to claim 1, and a physiologically compatible carrier.

8. The pharmaceutical composition according to claim 7, wherein the carrier is a buffered saline solution.

9. A vector comprising a nucleic acid sequence encoding microutrophin under the control of regulatory sequences which direct expression of the microutrophin in a host cell wherein the microutrophin is human microutrophin having the amino acid sequence of SEQ ID NO: 4.

10. The vector according to claim 9 wherein said vector is an adeno-associated viral vector.

11. A pharmaceutical composition comprising a vector according to claim 10 and a physiologically compatible carrier.

12. The pharmaceutical composition according to claim 11 wherein the carrier is a buffered saline solution.

13. A vector comprising a nucleic acid sequence encoding microutrophin under the control of regulatory sequences which direct expression of the microutrophin in a host cell wherein the microutrophin is canine microutrophin having the amino acid sequence of SEQ ID NO:2.

14. A vector comprising a nucleic acid sequence encoding microutrophin under the control of regulatory sequences which direct expression of the microutrophin in a host cell wherein the microutrophin is microutrophin having the amino acid sequence of SEQ ID NO:5.

* * * * *